US009561264B2

(12) United States Patent
Frank et al.

(10) Patent No.: US 9,561,264 B2
(45) Date of Patent: *Feb. 7, 2017

(54) GENE ENCODING A MULTIDRUG RESISTANCE HUMAN P-GLYCOPROTEIN HOMOLOGUE ON CHROMOSOME 7P15-21 AND USES THEREOF

(71) Applicant: The Brigham and Women's Hospital, Inc., Boston, MA (US)

(72) Inventors: Markus H. Frank, Cambridge, MA (US); Mohamed H. Sayegh, Westwood, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,938

(22) Filed: Jul. 10, 2013

(65) Prior Publication Data

US 2013/0287785 A1  Oct. 31, 2013

Related U.S. Application Data

(60) Continuation of application No. 13/279,549, filed on Oct. 24, 2011, now Pat. No. 8,507,273, which is a continuation of application No. 12/273,849, filed on Nov. 19, 2008, now Pat. No. 8,076,091, which is a continuation of application No. 10/952,328, filed on Sep. 29, 2004, now Pat. No. 7,465,554, which is a division of application No. 09/873,409, filed on Jun. 5, 2001, now Pat. No. 6,846,883.

(60) Provisional application No. 60/208,913, filed on Jun. 5, 2000.

(51) Int. Cl.

| A61K 38/17 | (2006.01) |
|---|---|
| A61K 39/00 | (2006.01) |
| A61K 39/395 | (2006.01) |
| C07K 16/28 | (2006.01) |
| C07K 14/705 | (2006.01) |
| A61K 38/00 | (2006.01) |
| A61K 48/00 | (2006.01) |

(52) U.S. Cl.
CPC ......... *A61K 39/0011* (2013.01); *C07K 14/705* (2013.01); *C07K 16/28* (2013.01); *A61K 38/00* (2013.01); *A61K 39/00* (2013.01); *A61K 48/00* (2013.01); *C07K 2317/34* (2013.01)

(58) Field of Classification Search
None
See application file for complete search history.

(56) References Cited

U.S. PATENT DOCUMENTS

| 5,399,483 | A | 3/1995 | Shibano et al. |
|---|---|---|---|
| 5,434,075 | A | 7/1995 | Mechetner et al. |
| 5,612,185 | A | 3/1997 | Uhr et al. |
| 6,008,002 | A | 12/1999 | Bodey |
| 6,355,239 | B1 | 3/2002 | Bruder et al. |
| 6,846,883 | B2 | 1/2005 | Frank et al. |
| 7,465,554 | B2 | 12/2008 | Frank et al. |
| 7,928,202 | B2 | 4/2011 | Frank et al. |
| 8,076,091 | B2 | 12/2011 | Frank et al. |
| 8,425,876 | B2 | 4/2013 | Frank et al. |
| 8,455,245 | B2 | 6/2013 | Frank et al. |
| 8,507,273 | B2 | 8/2013 | Frank et al. |
| 8,697,072 | B2 | 4/2014 | Frank et al. |
| 2007/0105133 | A1 | 5/2007 | Clarke et al. |
| 2008/0003206 | A1 | 1/2008 | Frank |
| 2008/0047026 | A1 | 2/2008 | Fuchs et al. |
| 2008/0118432 | A1 | 5/2008 | Bergstein et al. |
| 2008/0132423 | A1 | 6/2008 | Kondo |
| 2009/0117117 | A1 | 5/2009 | Frank et al. |
| 2009/0162873 | A1 | 6/2009 | Frank et al. |
| 2010/0145030 | A1 | 6/2010 | Frank et al. |
| 2010/0204458 | A1* | 8/2010 | Silva ................ A61K 38/1709 530/405 |
| 2011/0165149 | A1 | 7/2011 | Frank et al. |
| 2011/0287034 | A1 | 11/2011 | Frank et al. |
| 2012/0034196 | A1 | 2/2012 | Frank et al. |
| 2013/0315880 | A1 | 11/2013 | Frank et al. |
| 2014/0302031 | A1 | 10/2014 | Frank et al. |
| 2015/0374756 | A1 | 12/2015 | Frank et al. |
| 2016/0009804 | A1 | 1/2016 | Frank et al. |
| 2016/0106782 | A1 | 4/2016 | Frank et al. |
| 2016/0136297 | A1 | 5/2016 | Frank et al. |

FOREIGN PATENT DOCUMENTS

| EP | 0 174 810 | 3/1986 |
|---|---|---|
| EP | 0 267 781 | 5/1988 |
| EP | 10185365.3 | 2/2016 |
| EP | 14754427.4 | 8/2016 |
| WO | WO 93/25700 A1 | 12/1993 |
| WO | WO01/57273 * | 8/2001 |
| WO | WO 01/94400 A2 | 12/2001 |
| WO | WO 01/98361 A2 | 12/2001 |
| WO | WO 02/40541 | 5/2002 |
| WO | WO 2005/079145 A2 | 9/2005 |
| WO | WO 2006/103685 A2 | 10/2006 |
| WO | WO 2007/143139 | 12/2007 |

OTHER PUBLICATIONS

Nielsen et al, Cancer Chemotherapy and Pharmacology, 2000, vol. 46, supplement, pp. S62-S66.*

(Continued)

*Primary Examiner* — Karen Canella
(74) *Attorney, Agent, or Firm* — Wolf, Greenfield & Sacks, P.C.

(57) ABSTRACT

The invention relates to an MDR family P-glycoprotein located on human chromosome 7p15-21, polynucleotide sequences encoding this P-glycoprotein and fragments thereof. This gene is utilized in methods for assessing cancer cell susceptibility to therapies directed against multidrug resistance, and for the design of diagnostic and therapeutic methods relating to cancer multidrug resistance. The invention also relates to methods for determining whether a test compound may inhibit multidrug resistance.

5 Claims, No Drawings

(56) References Cited

OTHER PUBLICATIONS

Overwijk and Restifo, Trends in Immunology, 2001, vol. 22, pp. 5-7.*
Wheeler, Salud Publica de Mexico, 1997, pp. 1-5.*
Morrison et al, 'Complement activation and Fc receptor binding by IgG', In: Protein Engineering of antibody Molecules for Prophylactic and therapeutic applications in Man, 1993, Mike Clark, Ed., pp. 101-113.*
Schlom 'Monoclonal Antibodies: They're More and Less Than You Think', In: Molecular Foundations of Oncology, 1991, Samuel Broder, Ed, pp. 95-134.*
Sharom, Journal of Membrane Biology, 1997, vol. 160, pp. 161-175.*
Campbell (Monoclonal Antibody Technology, 1984, pp. 1-32).*
Dawson et al, Science, 1994, vol. 266, pp. 776-779).*
[No Author Listed] Genbank submission; NIH/NCBI; Accession No. AAA36207; Borst; Jun. 11, 1993.
Bork, Powers and pitfalls in sequence analysis: The 70% Hurdle. Genome Res. 2000 10:398-400.
Bork et al., Go hunting in sequence databases but watch out for traps. Trends in Genetics 1996, 12:425-427.
Bowie et al., Deciphering the message in protein sequences: tolerance to amino acid substitutions. Science 1990. 247:1306-1311.
Brenner, Errors in genome annotation. Trends in genetics 1999; 15:132-133.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. 1990; 111:2129-2138.
Chaudhary et al., Expression and activity of P-glycoprotein, a multidrug efflux pump, in human hematopoietic stem cells. Cell. Jul. 12, 1991;66(1):85-94.
Denner. Another anniversary for the war on cancer. Bio/Technology 1994. 12:320.
Doerks et al., Protein annotation: detective work for function prediction. Trends in Genetics 1998; 14:248-250.
EMBL/GenBank Submission; NIH/NCBI; Accession No. O14573; Kalicki; Mar. 1, 2002.
Frank et al., Regulation of progenitor cell fusion by ABCB5 P-Glycoprotein, a novel human ATP-binding cassette transporter. J Biol Chem 2003; 278:47156-47165.
Frank et al., ABCB5-Mediated Doxorubicin transport and chemoresistance in human malignant melanoma. Cancer Res. 2005;60;(10):4320-4333.
Frassoni et al., Cord blood transplantation provides better reconstitution of hematopoietic reservoir compared with bone marrow transplantation. Blood. Aug. 1, 2003;102(3):1138-41. Epub Apr. 10, 2003.
Freshney, Culture of animal cells, a manual of basic technique, Alan R. Liss, Inc. 1983, New York, p. 4.
GenBank Submission; NIH/NCBI; Accession No. AC005060; Waterston; Jun. 12, 1998.
GenBank Submission; NIH/NCBI; Accession No. AC005060; Sulston; Nov. 23, 2008.
GenBank Submission; NIH/NCBI, Accession No. AY234788; Frank et al.; Nov. 17, 2003.
Genbank Submission; NIH/NCBI, Accession No. NM_178559; Frank et al.; Nov. 17, 2006.
Genbank Submission; NIH/NCBI, Accession No. NP_848654; Frank et al.; Nov. 17, 2006.
Georges et al. Detection of P-Glycoprotein isoforms by gene-specific monoclonal antibodies. Proc Natl Acad Sci USA 1990; 87:152-156.
Gillet et al., Chemotherapy-induced resistance by ATP-binding cassette transporter genes. Biochim Biophys Acta. Jun. 2007; 1775(2):237-262. Epub Jun. 6, 2007.
Goodell et al., Isolation and functional properties of murine hematopoietic stem cells that are replicating in vivo. J Exp Med. Apr. 1, 1996;183(4):1797-1806.
Guerci et al., Predictive value for treatment outcome in acute myeloid leukemia of cellular daunorubicin accumulation and P-glycoprotein expression simultaneously determined by flow cytometry. Blood. Apr. 15, 1995;85(8):2147-53.
Kalicki et al., The sequence of H. sapiens BAC clone CTA-367017. EMBL/GenBank/DDBJ Databases (Abstract) 1997.
Knutsen et al., Cytogenetic and molecular characterization of random chromosomal rearrangements activating the drug resistance gene, MDR1/P-Glycoprotein, in drug-selected cell lines and patients with drug refractory ALL. Genes, Chromosomes & Cancer 1998; 23:44-54.
Lazar et al., Transforming growth factor α: mutation of aspartic acid 47 and leucine 48 results in different biological activities. Molecular and Cellular Biology 8 1988; 1247-1251.
Mechetner et al., Efficient inhibition of P-glycoprotein-mediated multidrug resistance with a monoclonal antibody. Proc Natl Acad Sci USA. Jul. 1, 1992;89(13):5824-5828.
Menke et al., Expression analysis of multidrug efflux pump genes in mouse hematopoietic stem and progenitor cells. Blood. 1999;94(10)(Supp 1, Part 1):Abstract #132.
Mickley et al., Gene rearrangements: a novel mechanism for MDR-1 gene activation. J Clin Invest 1997; 99:1947-1957.
Miwa et al., Biological characteristics of CD7(+) acute leukemia. Leuk Lymphoma. Apr. 1996;21(3-4):239-244.
Robert, Multidrug resistance in oncology; diagnostic and therapeutic approaches. Eur J Clin Invest. Jun. 1999;29(6):536-45.
Schoenlein et al., Double minute chromosomes carrying the human multidrug resistance 1 and 2 genes are generated from the dimerization of submicroscopic circular DNAs in colchicine-selected KB carcinoma cells. Mol Biol of the Cell. 1992; 3:507-520.
Scott et al., The pendred syndrome gene codes a chloride-iodide transport protein. Nature Genomics 1999. 21:440-443.
Sequence comparison cited in parent U.S. Appl. 09/873,409 (Apr. 20, 2003 Office Action).
Sequence comparison cited in parent U.S. Appl. No. 09/873,409 (Dec. 31, 2003 Office Action).
Skolnick et al. From genes to protein structure and function: novel applications of computational approaches in the genomic era. Trends in Biotech 2000 18:34-39.
Smith et al. The Challenges of genome sequence annotation or 'The Devil is in the Details' Nature Biotechnology 1997; 15:1222-1223.
Spangrude et al., Two mechanisms of discrimination between stem cells and progenitors by rhodamine-123: Mitochrondrial activation and multi-drug resistance. Blood. 1995;86(1)(Supp 1):Abstract #1830.
Storms et al., Isolation of primitive human hematopoietic progenitors on the basis of aldehyde dehydrogenase activity. Proc Natl Acad Sci USA. Aug. 3, 1999;96(16):9118-9123.
Young et al. (Proc Soc Exp Biol Med, 1999, vol. 221, pp. 63-72).
Cavallo et al., Vaccination for treatment and prevention of cancer in animal models. Adv Immunol. 2006;90:175-213. Abstract only.
Diaz-Borjon et al., Multidrug resistance-1 (MDR-1) in rheumatic autoimmune disorders. Part II: Increased P-glycoprotein activity in lymphocytes from systemic lupus erythematosus patients might affect steroid requirements for disease control. Joint Bone Spine. Jan. 2000;67(1):40-8. Abstract only.
Frank et al., Regulation of progenitor cell fusion by ABCB5 P-glycoprotein, a novel human ATP-binding cassette transporter. J Biol Chem. Nov. 21, 2003;278(47):47156-65. Epub Sep. 7, 2003.
Frank et al., ABCB5 P-glycoprotein is a molecular marker of the Hoechst 33342 side population phenotype among human fetal skeletal muscle cells. FASEB Journal. 2004;18(4-5):A183. Abstract 144.9.
Frank et al., Immunomodulatory functions of mesenchymal stem cells. Lancet. May 1, 2004;363(9419):1411-2.
Kim et al., Unmet need in lung cancer: can vaccines bridge the gap? Clin Lung Cancer. Feb. 2008;9 Suppl 1:S6-12.
Kleffel et al., ABCB5 inhibition sensitizes Merkel cell carcinoma cells to chemotherapy-induced apoptosis. J Invest Dermatol. 2014;134:S18. Meeting abstract.

(56) References Cited

OTHER PUBLICATIONS

Picchianti-Diamanti et al., P-glycoprotein and drug resistance in systemic autoimmune disease. Int J Mol Sci. Mar. 20, 2014;15(3):4965-76. doi: 10.3390/ijms15034965.
Notice of Allowance for U.S. Appl. No. 14/251,932, mailed Oct. 9, 2015.
Sayegh et al., The role of T-cell costimulatory activation pathways in transplant rejection. N Engl J Med. Jun. 18, 1998;338(25):1813-21.
European Office Communication mailed Feb. 22, 2016 for Application No. EP 10185365.3.
Extended European Search Report for EP 14754427.4 mailed Aug. 8, 2016.
Rama et al., Limbal stem-cell therapy and long-term corneal regeneration. N Engl J Med. Jul. 8, 2010;363(2):147-55. doi: 10.1056/NEJMoa0905955. Epub Jun. 23, 2010.
Schlötzer-Schrehardt et al., Identification and characterization of limbal stem cells. Exp Eye Res. Sep. 2005;81(3):247-64.
U.S. Appl. No. 13/832,419, filed Mar. 15, 2013, Frank.
U.S. Appl. No. 15/005,364, filed Jan. 25, 2016, Frank et al.

\* cited by examiner

SEQUENCE LISTING

```
<160> NUMBER OF SEQ ID NOS: 19

<210> SEQ ID NO 1
<211> LENGTH: 659
<212> TYPE: PRT
<213> ORGANISM: Homo sapiens

<400> SEQUENCE: 1

Met Leu Ala Glu Lys Gly Ala His Ala Glu Leu Met Ala Lys Arg Gly
1               5                   10                  15

Leu Tyr Tyr Ser Leu Val Met Ser Gln Asp Ile Lys Lys Ala Asp Glu
            20                  25                  30

Gln Met Glu Ser Met Thr Tyr Ser Thr Glu Arg Lys Thr Asn Ser Leu
        35                  40                  45

Pro Leu His Ser Val Lys Ser Ile Lys Ser Asp Phe Ile Asp Lys Ala
    50                  55                  60

Glu Glu Ser Thr Gln Ser Lys Glu Ile Ser Leu Pro Glu Val Ser Leu
65                  70                  75                  80

Leu Lys Ile Leu Lys Leu Asn Lys Pro Glu Trp Pro Phe Val Val Leu
                85                  90                  95

Gly Thr Leu Ala Ser Val Leu Asn Gly Thr Val His Pro Val Phe Ser
            100                 105                 110

Ile Ile Phe Ala Lys Ile Ile Thr Met Phe Gly Asn Asn Asp Lys Thr
        115                 120                 125

Thr Leu Lys His Asp Ala Glu Ile Tyr Ser Met Ile Phe Val Ile Leu
    130                 135                 140

Gly Val Ile Cys Phe Val Ser Tyr Phe Met Gln Gly Leu Phe Tyr Gly
145                 150                 155                 160

Arg Ala Gly Glu Ile Leu Thr Met Arg Leu Arg His Leu Ala Phe Lys
                165                 170                 175

Ala Met Leu Tyr Gln Asp Ile Ala Trp Phe Asp Glu Lys Glu Asn Ser
            180                 185                 190

Thr Gly Gly Leu Thr Thr Ile Leu Ala Ile Asp Ile Ala Gln Ile Gln
        195                 200                 205
```

-continued

```
Gly Ala Thr Gly Ser Arg Ile Gly Val Leu Thr Gln Asn Ala Thr Asn
    210                 215                 220
Met Gly Leu Ser Val Ile Ser Phe Ile Tyr Gly Trp Glu Met Thr
225                 230                 235                 240
Phe Leu Ile Leu Ser Ile Ala Pro Val Leu Ala Val Thr Gly Met Ile
                245                 250                 255
Glu Thr Ala Ala Met Thr Gly Phe Ala Asn Lys Asp Lys Gln Glu Leu
                260                 265                 270
Lys His Ala Gly Lys Ile Ala Thr Glu Ala Leu Glu Asn Ile Arg Thr
                275                 280                 285
Ile Val Ser Leu Thr Arg Glu Lys Ala Phe Glu Gln Met Tyr Glu Glu
                290                 295                 300
Met Leu Gln Thr Gln His Arg Asn Thr Ser Lys Lys Ala Gln Ile Ile
305                 310                 315                 320
Gly Ser Cys Tyr Ala Phe Ser His Ala Phe Ile Tyr Phe Ala Tyr Ala
                325                 330                 335
Ala Gly Phe Arg Phe Gly Ala Tyr Leu Ile Gln Ala Gly Arg Met Thr
                340                 345                 350
Pro Glu Gly Met Phe Ile Val Phe Thr Ala Ile Ala Tyr Gly Ala Met
                355                 360                 365
Ala Ile Gly Lys Thr Leu Val Leu Ala Pro Glu Tyr Ser Lys Ala Lys
                370                 375                 380
Ser Gly Ala Ala His Leu Phe Ala Leu Leu Glu Lys Lys Pro Asn Ile
385                 390                 395                 400
Asp Ser Arg Ser Gln Glu Gly Lys Lys Pro Asp Thr Cys Glu Gly Asn
                405                 410                 415
Leu Glu Phe Arg Glu Val Ser Phe Phe Tyr Pro Cys Arg Pro Asp Val
                420                 425                 430
Phe Ile Leu Arg Gly Leu Ser Leu Ser Ile Glu Arg Gly Lys Thr Val
                435                 440                 445
Ala Phe Val Gly Ser Ser Gly Cys Gly Lys Ser Thr Ser Val Gln Leu
450                 455                 460
Leu Gln Arg Leu Tyr Asp Pro Val Gln Gly Gln Val Leu Phe Asp Gly
465                 470                 475                 480
Val Asp Ala Lys Glu Leu Asn Val Gln Trp Leu Arg Ser Gln Ile Ala
                485                 490                 495
Ile Val Pro Gln Glu Pro Val Leu Phe Asn Cys Ser Ile Ala Glu Asn
                500                 505                 510
Ile Ala Tyr Gly Asp Asn Ser Arg Val Val Pro Leu Asp Glu Ile Lys
                515                 520                 525
Glu Ala Ala Asn Ala Ala Asn Ile His Ser Phe Ile Glu Gly Leu Pro
530                 535                 540
Glu Lys Tyr Asn Thr Gln Val Gly Leu Lys Gly Ala Gln Leu Ser Gly
545                 550                 555                 560
Gly Gln Lys Gln Arg Leu Ala Ile Ala Arg Ala Leu Leu Gln Lys Pro
                565                 570                 575
Lys Ile Leu Leu Leu Asp Glu Ala Thr Ser Ala Leu Asp Asn Asp Ser
                580                 585                 590
Glu Lys Val Val Gln His Ala Leu Asp Lys Ala Arg Thr Gly Arg Thr
                595                 600                 605
Cys Leu Val Val Thr His Arg Leu Ser Ala Ile Gln Asn Ala Asp Leu
610                 615                 620
```

```
Ile Val Val Leu His Asn Gly Lys Ile Lys Glu Gln Gly Thr His Gln
625                 630                 635                 640

Glu Leu Leu Arg Asn Arg Asp Ile Tyr Phe Lys Leu Val Asn Ala Gln
            645                 650                 655

Ser Val Gln

<210> SEQ ID NO 2
<211> LENGTH: 812
<212> TYPE: PRT
<213> ORGANISM: Homo sapiens

<400> SEQUENCE: 2

Met Val Asp Glu Asn Asp Ile Arg Ala Leu Asn Val Arg His Tyr Arg
1               5                   10                  15

Asp His Ile Gly Val Val Ser Gln Glu Pro Val Leu Phe Gly Thr Thr
                20                  25                  30

Ile Ser Asn Asn Ile Lys Tyr Gly Arg Asp Asp Val Thr Asp Glu Glu
            35                  40                  45

Met Glu Arg Ala Ala Arg Glu Ala Asn Ala Tyr Asp Phe Ile Met Glu
    50                  55                  60

Phe Pro Asn Lys Phe Asn Thr Leu Val Gly Glu Lys Gly Ala Gln Met
65                  70                  75                  80

Ser Gly Gly Gln Lys Gln Arg Ile Ala Ile Ala Arg Ala Leu Val Arg
                85                  90                  95

Asn Pro Lys Ile Leu Ile Leu Asp Glu Ala Thr Ser Ala Leu Asp Ser
            100                 105                 110

Glu Ser Lys Ser Ala Val Gln Ala Leu Glu Lys Ala Ser Lys Gly
    115                 120                 125

Arg Thr Thr Ile Val Val Ala His Arg Leu Ser Thr Ile Arg Ser Ala
130                 135                 140

Asp Leu Ile Val Thr Leu Lys Asp Gly Met Leu Ala Glu Lys Gly Ala
145                 150                 155                 160

His Ala Glu Leu Met Ala Lys Arg Gly Leu Tyr Tyr Ser Leu Val Met
                165                 170                 175

Ser Gln Asp Ile Lys Lys Ala Asp Glu Gln Met Glu Ser Met Thr Tyr
            180                 185                 190

Ser Thr Glu Arg Lys Thr Asn Ser Leu Pro Leu His Ser Val Lys Ser
    195                 200                 205

Ile Lys Ser Asp Phe Ile Asp Lys Ala Glu Glu Ser Thr Gln Ser Lys
210                 215                 220

Glu Ile Ser Leu Pro Glu Val Ser Leu Leu Lys Ile Leu Lys Leu Asn
225                 230                 235                 240

Lys Pro Glu Trp Pro Phe Val Val Leu Gly Thr Leu Ala Ser Val Leu
                245                 250                 255

Asn Gly Thr Val His Pro Val Phe Ser Ile Ile Phe Ala Lys Ile Ile
            260                 265                 270

Thr Met Phe Gly Asn Asn Asp Lys Thr Thr Leu Lys His Asp Ala Glu
    275                 280                 285

Ile Tyr Ser Met Ile Phe Val Ile Leu Gly Val Ile Cys Phe Val Ser
290                 295                 300

Tyr Phe Met Gln Gly Leu Phe Tyr Gly Arg Ala Gly Glu Ile Leu Thr
305                 310                 315                 320

Met Arg Leu Arg His Leu Ala Phe Lys Ala Met Leu Tyr Gln Asp Ile
                325                 330                 335
```

```
Ala Trp Phe Asp Glu Lys Glu Asn Ser Thr Gly Gly Leu Thr Thr Ile
                340                 345                 350

Leu Ala Ile Asp Ile Ala Gln Ile Gln Gly Ala Thr Gly Ser Arg Ile
            355                 360                 365

Gly Val Leu Thr Gln Asn Ala Thr Asn Met Gly Leu Ser Val Ile Ile
        370                 375                 380

Ser Phe Ile Tyr Gly Trp Glu Met Thr Phe Leu Ile Leu Ser Ile Ala
385                 390                 395                 400

Pro Val Leu Ala Val Thr Gly Met Ile Glu Thr Ala Ala Met Thr Gly
                405                 410                 415

Phe Ala Asn Lys Asp Lys Gln Glu Leu Lys His Ala Gly Lys Ile Ala
            420                 425                 430

Thr Glu Ala Leu Glu Asn Ile Arg Thr Ile Val Ser Leu Thr Arg Glu
        435                 440                 445

Lys Ala Phe Glu Gln Met Tyr Glu Glu Met Leu Gln Thr Gln His Arg
450                 455                 460

Asn Thr Ser Lys Lys Ala Gln Ile Ile Gly Ser Cys Tyr Ala Phe Ser
465                 470                 475                 480

His Ala Phe Ile Tyr Phe Ala Tyr Ala Ala Gly Phe Arg Phe Gly Ala
            485                 490                 495

Tyr Leu Ile Gln Ala Gly Arg Met Thr Pro Glu Gly Met Phe Ile Val
        500                 505                 510

Phe Thr Ala Ile Ala Tyr Gly Ala Met Ala Ile Gly Lys Thr Leu Val
            515                 520                 525

Leu Ala Pro Glu Tyr Ser Lys Ala Lys Ser Gly Ala Ala His Leu Phe
530                 535                 540

Ala Leu Leu Glu Lys Lys Pro Asn Ile Asp Ser Arg Ser Gln Glu Gly
545                 550                 555                 560

Lys Lys Pro Asp Thr Cys Glu Gly Asn Leu Glu Phe Arg Glu Val Ser
            565                 570                 575

Phe Phe Tyr Pro Cys Arg Pro Asp Val Phe Ile Leu Arg Gly Leu Ser
            580                 585                 590

Leu Ser Ile Glu Arg Gly Lys Thr Val Ala Phe Val Gly Ser Ser Gly
        595                 600                 605

Cys Gly Lys Ser Thr Ser Val Gln Leu Leu Gln Arg Leu Tyr Asp Pro
        610                 615                 620

Val Gln Gly Gln Val Leu Phe Asp Gly Val Asp Ala Lys Glu Leu Asn
625                 630                 635                 640

Val Gln Trp Leu Arg Ser Gln Ile Ala Ile Val Pro Gln Glu Pro Val
            645                 650                 655

Leu Phe Asn Cys Ser Ile Ala Glu Asn Ile Ala Tyr Gly Asp Asn Ser
            660                 665                 670

Arg Val Val Pro Leu Asp Glu Ile Lys Glu Ala Ala Asn Ala Ala Asn
        675                 680                 685

Ile His Ser Phe Ile Glu Gly Leu Pro Glu Lys Tyr Asn Thr Gln Val
        690                 695                 700

Gly Leu Lys Gly Ala Gln Leu Ser Gly Gly Gln Lys Gln Arg Leu Ala
705                 710                 715                 720

Ile Ala Arg Ala Leu Leu Lys Pro Lys Ile Leu Leu Leu Asp Glu
                725                 730                 735

Ala Thr Ser Ala Leu Asp Asn Asp Ser Glu Lys Val Val Gln His Ala
            740                 745                 750

Leu Asp Lys Ala Arg Thr Gly Arg Thr Cys Leu Val Val Thr His Arg
```

```
                755                 760                 765
Leu Ser Ala Ile Gln Asn Ala Asp Leu Ile Val Val Leu His Asn Gly
    770                 775                 780
Lys Ile Lys Glu Gln Gly Thr His Gln Glu Leu Leu Arg Asn Arg Asp
785                 790                 795                 800
Ile Tyr Phe Lys Leu Val Asn Ala Gln Ser Val Gln
                805                 810

<210> SEQ ID NO 3
<211> LENGTH: 131
<212> TYPE: PRT
<213> ORGANISM: Homo sapiens

<400> SEQUENCE: 3

Met Val Asp Glu Asn Asp Ile Arg Ala Leu Asn Val Arg His Tyr Arg
1               5                   10                  15
Asp His Ile Gly Val Val Ser Gln Glu Pro Val Leu Phe Gly Thr Thr
                20                  25                  30
Ile Ser Asn Asn Ile Lys Tyr Gly Arg Asp Asp Val Thr Asp Glu Glu
            35                  40                  45
Met Glu Arg Ala Ala Arg Glu Ala Asn Ala Tyr Asp Phe Ile Met Glu
        50                  55                  60
Phe Pro Asn Lys Phe Asn Thr Leu Val Gly Glu Lys Gly Ala Gln Met
65                  70                  75                  80
Ser Gly Gly Gln Lys Gln Arg Ile Ala Ile Ala Arg Ala Leu Val Arg
                85                  90                  95
Asn Pro Lys Ile Leu Ile Leu Asp Glu Ala Thr Ser Ala Leu Asp Ser
                100                 105                 110
Glu Ser Lys Ser Ala Val Gln Ala Ala Leu Glu Lys Asp Thr Pro Arg
            115                 120                 125
Tyr Ser Phe
        130

<210> SEQ ID NO 4
<211> LENGTH: 1058
<212> TYPE: PRT
<213> ORGANISM: Homo sapiens
<220> FEATURE:
<221> NAME/KEY: MISC_FEATURE
<222> LOCATION: (66)..(66)
<223> OTHER INFORMATION: Xaa at position 66 represents any L amino acid

<400> SEQUENCE: 4

Met Val Ile Ser Leu Thr Ser Lys Glu Leu Ser Ala Tyr Ser Lys Ala
1               5                   10                  15
Gly Ala Val Ala Glu Glu Val Leu Ser Ser Ile Arg Thr Val Ile Ala
                20                  25                  30
Phe Arg Ala Gln Glu Lys Glu Leu Gln Arg Ser Phe Leu Leu Asn Ile
            35                  40                  45
Thr Arg Tyr Ala Trp Phe Tyr Phe Pro Gln Trp Leu Leu Ser Cys Val
        50                  55                  60
Leu Xaa Phe Val Arg Tyr Thr Gln Asn Leu Lys Asp Ala Lys Asp Phe
65                  70                  75                  80
Gly Ile Lys Arg Thr Ile Ala Ser Lys Val Ser Leu Gly Ala Val Tyr
                85                  90                  95
Phe Phe Met Asn Gly Tyr Gly Leu Ala Phe Trp Tyr Gly Thr Ser
                100                 105                 110
```

```
Leu Ile Leu Asn Gly Glu Pro Gly Tyr Thr Ile Gly Thr Val Leu Ala
        115                 120                 125

Val Phe Phe Ser Val Ile His Ser Ser Tyr Cys Ile Gly Ala Ala Val
130                 135                 140

Pro His Phe Glu Thr Phe Ala Ile Ala Arg Gly Ala Ala Phe His Ile
145                 150                 155                 160

Phe Gln Val Ile Asp Lys Lys Pro Ser Ile Asp Asn Phe Ser Thr Ala
                165                 170                 175

Gly Tyr Lys Pro Glu Ser Ile Glu Gly Thr Val Glu Phe Lys Asn Val
            180                 185                 190

Ser Phe Asn Tyr Pro Ser Arg Pro Ser Ile Lys Ile Leu Lys Gly Leu
        195                 200                 205

Asn Leu Arg Ile Lys Ser Gly Glu Thr Val Ala Leu Val Gly Leu Asn
210                 215                 220

Gly Ser Gly Lys Ser Thr Val Val Gln Leu Leu Gln Arg Leu Tyr Asp
225                 230                 235                 240

Pro Asp Asp Gly Phe Ile Met Val Asp Glu Asn Asp Ile Arg Ala Leu
                245                 250                 255

Asn Val Arg His Tyr Arg Asp His Ile Gly Val Val Ser Gln Glu Pro
            260                 265                 270

Val Leu Phe Gly Thr Thr Ile Ser Asn Asn Ile Lys Tyr Gly Arg Asp
        275                 280                 285

Asp Val Thr Asp Glu Glu Met Glu Arg Ala Ala Arg Glu Ala Asn Ala
    290                 295                 300

Tyr Asp Phe Ile Met Glu Phe Pro Asn Lys Phe Asn Thr Leu Val Gly
305                 310                 315                 320

Glu Lys Gly Ala Gln Met Ser Gly Gly Gln Lys Gln Arg Ile Ala Ile
                325                 330                 335

Ala Arg Ala Leu Val Arg Asn Pro Lys Ile Leu Ile Leu Asp Glu Ala
            340                 345                 350

Thr Ser Ala Leu Asp Ser Glu Ser Lys Ser Ala Val Gln Ala Ala Leu
        355                 360                 365

Glu Lys Ala Ser Lys Gly Arg Thr Thr Ile Val Val Ala His Arg Leu
370                 375                 380

Ser Thr Ile Arg Ser Ala Asp Leu Ile Val Thr Leu Lys Asp Gly Met
385                 390                 395                 400

Leu Ala Glu Lys Gly Ala His Ala Glu Leu Met Ala Lys Arg Gly Leu
                405                 410                 415

Tyr Tyr Ser Leu Val Met Ser Gln Asp Ile Lys Lys Ala Asp Glu Gln
            420                 425                 430

Met Glu Ser Met Thr Tyr Ser Thr Glu Arg Lys Thr Asn Ser Leu Pro
        435                 440                 445

Leu His Ser Val Lys Ser Ile Lys Ser Asp Phe Ile Asp Lys Ala Glu
        450                 455                 460

Glu Ser Thr Gln Ser Lys Glu Ile Ser Leu Pro Glu Val Ser Leu Leu
465                 470                 475                 480

Lys Ile Leu Lys Leu Asn Lys Pro Glu Trp Pro Phe Val Val Leu Gly
                485                 490                 495

Thr Leu Ala Ser Val Leu Asn Gly Thr Val His Pro Val Phe Ser Ile
            500                 505                 510

Ile Phe Ala Lys Ile Ile Thr Met Phe Gly Asn Asn Asp Lys Thr Thr
        515                 520                 525

Leu Lys His Asp Ala Glu Ile Tyr Ser Met Ile Phe Val Ile Leu Gly
```

-continued

```
                530                 535                 540
Val Ile Cys Phe Val Ser Tyr Phe Met Gln Gly Leu Phe Tyr Gly Arg
545                 550                 555                 560

Ala Gly Glu Ile Leu Thr Met Arg Leu Arg His Leu Ala Phe Lys Ala
                565                 570                 575

Met Leu Tyr Gln Asp Ile Ala Trp Phe Asp Glu Lys Glu Asn Ser Thr
                580                 585                 590

Gly Gly Leu Thr Thr Ile Leu Ala Ile Asp Ile Ala Gln Ile Gln Gly
                595                 600                 605

Ala Thr Gly Ser Arg Ile Gly Val Leu Thr Gln Asn Ala Thr Asn Met
610                 615                 620

Gly Leu Ser Val Ile Ile Ser Phe Ile Tyr Gly Trp Glu Met Thr Phe
625                 630                 635                 640

Leu Ile Leu Ser Ile Ala Pro Val Leu Ala Val Thr Gly Met Ile Glu
                645                 650                 655

Thr Ala Ala Met Thr Gly Phe Ala Asn Lys Asp Lys Gln Glu Leu Lys
                660                 665                 670

His Ala Gly Lys Ile Ala Thr Glu Ala Leu Glu Asn Ile Arg Thr Ile
                675                 680                 685

Val Ser Leu Thr Arg Glu Lys Ala Phe Glu Gln Met Tyr Glu Glu Met
                690                 695                 700

Leu Gln Thr Gln His Arg Asn Thr Ser Lys Lys Ala Gln Ile Ile Gly
705                 710                 715                 720

Ser Cys Tyr Ala Phe Ser His Ala Phe Ile Tyr Phe Ala Tyr Ala Ala
                725                 730                 735

Gly Phe Arg Phe Gly Ala Tyr Leu Ile Gln Ala Gly Arg Met Thr Pro
                740                 745                 750

Glu Gly Met Phe Ile Val Phe Thr Ala Ile Ala Tyr Gly Ala Met Ala
                755                 760                 765

Ile Gly Lys Thr Leu Val Leu Ala Pro Glu Tyr Ser Lys Ala Lys Ser
                770                 775                 780

Gly Ala Ala His Leu Phe Ala Leu Leu Glu Lys Lys Pro Asn Ile Asp
785                 790                 795                 800

Ser Arg Ser Gln Glu Gly Lys Lys Pro Asp Thr Cys Glu Gly Asn Leu
                805                 810                 815

Glu Phe Arg Glu Val Ser Phe Tyr Pro Cys Arg Pro Asp Val Phe
                820                 825                 830

Ile Leu Arg Gly Leu Ser Leu Ser Ile Glu Arg Gly Lys Thr Val Ala
                835                 840                 845

Phe Val Gly Ser Ser Gly Cys Gly Lys Ser Thr Ser Val Gln Leu Leu
850                 855                 860

Gln Arg Leu Tyr Asp Pro Val Gln Gly Gln Val Leu Phe Asp Gly Val
865                 870                 875                 880

Asp Ala Lys Glu Leu Asn Val Gln Trp Leu Arg Ser Gln Ile Ala Ile
                885                 890                 895

Val Pro Gln Glu Pro Val Leu Phe Asn Cys Ser Ile Ala Glu Asn Ile
                900                 905                 910

Ala Tyr Gly Asp Asn Ser Arg Val Val Pro Leu Asp Glu Ile Lys Glu
                915                 920                 925

Ala Ala Asn Ala Ala Asn Ile His Ser Phe Ile Glu Gly Leu Pro Glu
                930                 935                 940

Lys Tyr Asn Thr Gln Val Gly Leu Lys Gly Ala Gln Leu Ser Gly Gly
945                 950                 955                 960
```

```
Gln Lys Gln Arg Leu Ala Ile Arg Ala Leu Leu Gln Lys Pro Lys
            965                 970                 975

Ile Leu Leu Leu Asp Glu Ala Thr Ser Ala Leu Asp Asn Asp Ser Glu
            980                 985                 990

Lys Val Val Gln His Ala Leu Asp Lys Ala Arg Thr Gly Arg Thr Cys
            995                1000                1005

Leu Val Val Thr His Arg Leu Ser Ala Ile Gln Asn Ala Asp Leu
       1010                1015                1020

Ile Val Val Leu His Asn Gly Lys Ile Lys Glu Gln Gly Thr His
       1025                1030                1035

Gln Glu Leu Leu Arg Asn Arg Asp Ile Tyr Phe Lys Leu Val Asn
       1040                1045                1050

Ala Gln Ser Val Gln
       1055

<210> SEQ ID NO 5
<211> LENGTH: 1222
<212> TYPE: PRT
<213> ORGANISM: Homo sapiens
<220> FEATURE:
<221> NAME/KEY: MISC_FEATURE
<222> LOCATION: (230)..(230)
<223> OTHER INFORMATION: Xaa at position 230 represents any L amino acid

<400> SEQUENCE: 5

Met Ile Leu Gly Ile Leu Ala Ser Leu Val Asn Gly Ala Cys Leu Pro
1               5                   10                  15

Leu Met Pro Leu Val Leu Gly Glu Met Ser Asp Asn Leu Ile Ser Gly
            20                  25                  30

Cys Leu Val Gln Thr Asn Thr Tyr Ser Phe Phe Arg Leu Thr Leu Tyr
        35                  40                  45

Tyr Val Gly Ile Gly Val Ala Ala Leu Ile Phe Gly Tyr Ile Gln Ile
    50                  55                  60

Ser Leu Trp Ile Ile Thr Ala Ala Arg Gln Thr Lys Arg Ile Arg Lys
65                  70                  75                  80

Gln Phe Phe His Ser Val Leu Ala Gln Asp Ile Gly Trp Phe Asp Ser
                85                  90                  95

Cys Asp Ile Gly Glu Leu Asn Thr Arg Met Thr Asp Ile Asp Lys Ile
            100                 105                 110

Ser Asp Gly Ile Gly Asp Lys Ile Ala Leu Leu Phe Gln Asn Met Ser
        115                 120                 125

Thr Phe Ser Ile Gly Leu Ala Val Gly Leu Val Lys Gly Trp Lys Leu
    130                 135                 140

Thr Leu Val Thr Leu Ser Thr Ser Pro Leu Ile Met Ala Ser Ala Ala
145                 150                 155                 160

Ala Cys Ser Arg Met Val Ile Ser Leu Thr Ser Lys Glu Leu Ser Ala
                165                 170                 175

Tyr Ser Lys Ala Gly Ala Val Ala Glu Val Leu Ser Ser Ile Arg
            180                 185                 190

Thr Val Ile Ala Phe Arg Ala Gln Glu Lys Glu Leu Gln Arg Ser Phe
        195                 200                 205

Leu Leu Asn Ile Thr Arg Tyr Ala Trp Phe Tyr Phe Pro Gln Trp Leu
    210                 215                 220

Leu Ser Cys Val Leu Xaa Phe Val Arg Tyr Thr Gln Asn Leu Lys Asp
225                 230                 235                 240
```

-continued

```
Ala Lys Asp Phe Gly Ile Lys Arg Thr Ile Ala Ser Lys Val Ser Leu
            245                 250                 255

Gly Ala Val Tyr Phe Phe Met Asn Gly Thr Tyr Gly Leu Ala Phe Trp
        260                 265                 270

Tyr Gly Thr Ser Leu Ile Leu Asn Gly Glu Pro Gly Tyr Thr Ile Gly
        275                 280                 285

Thr Val Leu Ala Val Phe Phe Ser Val Ile His Ser Ser Tyr Cys Ile
290                 295                 300

Gly Ala Ala Val Pro His Phe Glu Thr Phe Ala Ile Ala Arg Gly Ala
305                 310                 315                 320

Ala Phe His Ile Phe Gln Val Ile Asp Lys Lys Pro Ser Ile Asp Asn
                325                 330                 335

Phe Ser Thr Ala Gly Tyr Lys Pro Glu Ser Ile Glu Gly Thr Val Glu
            340                 345                 350

Phe Lys Asn Val Ser Phe Asn Tyr Pro Ser Arg Pro Ser Ile Lys Ile
        355                 360                 365

Leu Lys Gly Leu Asn Leu Arg Ile Lys Ser Gly Glu Thr Val Ala Leu
    370                 375                 380

Val Gly Leu Asn Gly Ser Gly Lys Ser Thr Val Val Gln Leu Leu Gln
385                 390                 395                 400

Arg Leu Tyr Asp Pro Asp Asp Gly Phe Ile Met Val Asp Glu Asn Asp
                405                 410                 415

Ile Arg Ala Leu Asn Val Arg His Tyr Arg Asp His Ile Gly Val Val
            420                 425                 430

Ser Gln Glu Pro Val Leu Phe Gly Thr Thr Ile Ser Asn Asn Ile Lys
        435                 440                 445

Tyr Gly Arg Asp Asp Val Thr Asp Glu Glu Met Glu Arg Ala Ala Arg
    450                 455                 460

Glu Ala Asn Ala Tyr Asp Phe Ile Met Glu Phe Pro Asn Lys Phe Asn
465                 470                 475                 480

Thr Leu Val Gly Glu Lys Gly Ala Gln Met Ser Gly Gly Gln Lys Gln
                485                 490                 495

Arg Ile Ala Ile Ala Arg Ala Leu Val Arg Asn Pro Lys Ile Leu Ile
            500                 505                 510

Leu Asp Glu Ala Thr Ser Ala Leu Asp Ser Glu Ser Lys Ser Ala Val
        515                 520                 525

Gln Ala Ala Leu Glu Lys Ala Ser Lys Gly Arg Thr Thr Ile Val Val
    530                 535                 540

Ala His Arg Leu Ser Thr Ile Arg Ser Ala Asp Leu Ile Val Thr Leu
545                 550                 555                 560

Lys Asp Gly Met Leu Ala Glu Lys Gly Ala His Ala Glu Leu Met Ala
                565                 570                 575

Lys Arg Gly Leu Tyr Tyr Ser Leu Val Met Ser Gln Asp Ile Lys Lys
            580                 585                 590

Ala Asp Glu Gln Met Glu Ser Met Thr Tyr Ser Thr Glu Arg Lys Thr
        595                 600                 605

Asn Ser Leu Pro Leu His Ser Val Lys Ser Ile Lys Ser Asp Phe Ile
    610                 615                 620

Asp Lys Ala Glu Glu Ser Thr Gln Ser Lys Glu Ile Ser Leu Pro Glu
625                 630                 635                 640

Val Ser Leu Leu Lys Ile Leu Lys Leu Asn Lys Pro Glu Trp Pro Phe
                645                 650                 655

Val Val Leu Gly Thr Leu Ala Ser Val Leu Asn Gly Thr Val His Pro
```

-continued

```
            660                 665                 670
Val Phe Ser Ile Ile Phe Ala Lys Ile Ile Thr Met Phe Gly Asn Asn
        675                 680                 685
Asp Lys Thr Thr Leu Lys His Asp Ala Glu Ile Tyr Ser Met Ile Phe
        690                 695                 700
Val Ile Leu Gly Val Ile Cys Phe Val Ser Tyr Phe Met Gln Gly Leu
705                 710                 715                 720
Phe Tyr Gly Arg Ala Gly Glu Ile Leu Thr Met Arg Leu Arg His Leu
                725                 730                 735
Ala Phe Lys Ala Met Leu Tyr Gln Asp Ile Ala Trp Phe Asp Glu Lys
            740                 745                 750
Glu Asn Ser Thr Gly Gly Leu Thr Thr Ile Leu Ala Ile Asp Ile Ala
            755                 760                 765
Gln Ile Gln Gly Ala Thr Gly Ser Arg Ile Gly Val Leu Thr Gln Asn
            770                 775                 780
Ala Thr Asn Met Gly Leu Ser Val Ile Ile Ser Phe Ile Tyr Gly Trp
785                 790                 795                 800
Glu Met Thr Phe Leu Ile Leu Ser Ile Ala Pro Val Leu Ala Val Thr
                805                 810                 815
Gly Met Ile Glu Thr Ala Ala Met Thr Gly Phe Ala Asn Lys Asp Lys
            820                 825                 830
Gln Glu Leu Lys His Ala Gly Lys Ile Ala Thr Glu Ala Leu Glu Asn
            835                 840                 845
Ile Arg Thr Ile Val Ser Leu Thr Arg Glu Lys Ala Phe Glu Gln Met
850                 855                 860
Tyr Glu Glu Met Leu Gln Thr Gln His Arg Asn Thr Ser Lys Lys Ala
865                 870                 875                 880
Gln Ile Ile Gly Ser Cys Tyr Ala Phe Ser His Ala Phe Ile Tyr Phe
                885                 890                 895
Ala Tyr Ala Ala Gly Phe Arg Phe Gly Ala Tyr Leu Ile Gln Ala Gly
                900                 905                 910
Arg Met Thr Pro Glu Gly Met Phe Ile Val Phe Thr Ala Ile Ala Tyr
            915                 920                 925
Gly Ala Met Ala Ile Gly Lys Thr Leu Val Leu Ala Pro Glu Tyr Ser
            930                 935                 940
Lys Ala Lys Ser Gly Ala Ala His Leu Phe Ala Leu Leu Glu Lys Lys
945                 950                 955                 960
Pro Asn Ile Asp Ser Arg Ser Gln Glu Gly Lys Lys Pro Asp Thr Cys
                965                 970                 975
Glu Gly Asn Leu Glu Phe Arg Glu Val Ser Phe Phe Tyr Pro Cys Arg
            980                 985                 990
Pro Asp Val Phe Ile Leu Arg Gly Leu Ser Leu Ser Ile Glu Arg Gly
                995                 1000                1005
Lys Thr Val Ala Phe Val Gly Ser Ser Gly Cys Gly Lys Ser Thr
        1010                1015                1020
Ser Val Gln Leu Leu Gln Arg Leu Tyr Asp Pro Val Gln Gly Gln
        1025                1030                1035
Val Leu Phe Asp Gly Val Asp Ala Lys Glu Leu Asn Val Gln Trp
        1040                1045                1050
Leu Arg Ser Gln Ile Ala Ile Val Pro Gln Glu Pro Val Leu Phe
        1055                1060                1065
Asn Cys Ser Ile Ala Glu Asn Ile Ala Tyr Gly Asp Asn Ser Arg
        1070                1075                1080
```

```
Val Val Pro Leu Asp Glu Ile Lys Glu Ala Ala Asn Ala Ala Asn
    1085                1090                1095

Ile His Ser Phe Ile Glu Gly Leu Pro Glu Lys Tyr Asn Thr Gln
    1100                1105                1110

Val Gly Leu Lys Gly Ala Gln Leu Ser Gly Gly Gln Lys Gln Arg
    1115                1120                1125

Leu Ala Ile Ala Arg Ala Leu Leu Gln Lys Pro Lys Ile Leu Leu
    1130                1135                1140

Leu Asp Glu Ala Thr Ser Ala Leu Asp Asn Asp Ser Glu Lys Val
    1145                1150                1155

Val Gln His Ala Leu Asp Lys Ala Arg Thr Gly Arg Thr Cys Leu
    1160                1165                1170

Val Val Thr His Arg Leu Ser Ala Ile Gln Asn Ala Asp Leu Ile
    1175                1180                1185

Val Val Leu His Asn Gly Lys Ile Lys Glu Gln Gly Thr His Gln
    1190                1195                1200

Glu Leu Leu Arg Asn Arg Asp Ile Tyr Phe Lys Leu Val Asn Ala
    1205                1210                1215

Gln Ser Val Gln
    1220

<210> SEQ ID NO 6
<211> LENGTH: 1195
<212> TYPE: PRT
<213> ORGANISM: Homo sapiens

<400> SEQUENCE: 6

Met Ile Leu Gly Ile Leu Ala Ser Leu Val Asn Gly Ala Cys Leu Pro
1                   5                   10                  15

Leu Met Pro Leu Val Leu Gly Glu Met Ser Asp Asn Leu Ile Ser Gly
                20                  25                  30

Cys Leu Val Gln Thr Asn Thr Tyr Ser Phe Phe Arg Leu Thr Leu Tyr
            35                  40                  45

Tyr Val Gly Ile Gly Val Ala Ala Leu Ile Phe Gly Tyr Ile Gln Ile
        50                  55                  60

Ser Leu Trp Ile Ile Thr Ala Ala Arg Gln Thr Lys Arg Ile Arg Lys
65                  70                  75                  80

Gln Phe Phe His Ser Val Leu Ala Gln Asp Ile Gly Trp Phe Asp Ser
                85                  90                  95

Cys Asp Ile Gly Glu Leu Asn Thr Arg Met Thr Asp Ile Asp Lys Ile
            100                 105                 110

Ser Asp Gly Ile Gly Asp Lys Ile Ala Leu Leu Phe Gln Asn Met Ser
        115                 120                 125

Thr Phe Ser Ile Gly Leu Ala Val Gly Leu Val Lys Gly Trp Lys Leu
    130                 135                 140

Thr Leu Val Thr Leu Ser Thr Ser Pro Leu Ile Met Ala Ser Ala Ala
145                 150                 155                 160

Ala Cys Ser Arg Met Val Ile Ser Leu Thr Ser Lys Glu Leu Ser Ala
                165                 170                 175

Tyr Ser Lys Ala Gly Ala Val Ala Glu Glu Val Leu Ser Ser Ile Arg
            180                 185                 190

Thr Val Ile Ala Phe Arg Ala Gln Glu Lys Glu Leu Gln Arg Tyr Thr
        195                 200                 205

Gln Asn Leu Lys Asp Ala Lys Asp Phe Gly Ile Lys Arg Thr Ile Ala
```

-continued

```
            210                 215                 220
Ser Lys Val Ser Leu Gly Ala Val Tyr Phe Phe Met Asn Gly Thr Tyr
225                 230                 235                 240

Gly Leu Ala Phe Trp Tyr Gly Thr Ser Leu Ile Leu Asn Gly Glu Pro
                245                 250                 255

Gly Tyr Thr Ile Gly Thr Val Leu Ala Val Phe Phe Ser Val Ile His
                260                 265                 270

Ser Ser Tyr Cys Ile Gly Ala Ala Val Pro His Phe Glu Thr Phe Ala
            275                 280                 285

Ile Ala Arg Gly Ala Ala Phe His Ile Phe Gln Val Ile Asp Lys Lys
        290                 295                 300

Pro Ser Ile Asp Asn Phe Ser Thr Ala Gly Tyr Lys Pro Glu Ser Ile
305                 310                 315                 320

Glu Gly Thr Val Glu Phe Lys Asn Val Ser Phe Asn Tyr Pro Ser Arg
                325                 330                 335

Pro Ser Ile Lys Ile Leu Lys Gly Leu Asn Leu Arg Ile Lys Ser Gly
                340                 345                 350

Glu Thr Val Ala Leu Val Gly Leu Asn Gly Ser Gly Lys Ser Thr Val
            355                 360                 365

Val Gln Leu Leu Gln Arg Leu Tyr Asp Pro Asp Asp Gly Phe Ile Met
        370                 375                 380

Val Asp Glu Asn Asp Ile Arg Ala Leu Asn Val Arg His Tyr Arg Asp
385                 390                 395                 400

His Ile Gly Val Val Ser Gln Glu Pro Val Leu Phe Gly Thr Thr Ile
                405                 410                 415

Ser Asn Asn Ile Lys Tyr Gly Arg Asp Asp Val Thr Asp Glu Glu Met
                420                 425                 430

Glu Arg Ala Ala Arg Glu Ala Asn Ala Tyr Asp Phe Ile Met Glu Phe
            435                 440                 445

Pro Asn Lys Phe Asn Thr Leu Val Gly Glu Lys Gly Ala Gln Met Ser
450                 455                 460

Gly Gly Gln Lys Gln Arg Ile Ala Ile Ala Arg Ala Leu Val Arg Asn
465                 470                 475                 480

Pro Lys Ile Leu Ile Leu Asp Glu Ala Thr Ser Ala Leu Asp Ser Glu
                485                 490                 495

Ser Lys Ser Ala Val Gln Ala Ala Leu Glu Lys Ala Ser Lys Gly Arg
            500                 505                 510

Thr Thr Ile Val Val Ala His Arg Leu Ser Thr Ile Arg Ser Ala Asp
        515                 520                 525

Leu Ile Val Thr Leu Lys Asp Gly Met Leu Ala Glu Lys Gly Ala His
530                 535                 540

Ala Glu Leu Met Ala Lys Arg Gly Leu Tyr Tyr Ser Leu Val Met Ser
545                 550                 555                 560

Gln Asp Ile Lys Lys Ala Asp Glu Gln Met Glu Ser Met Thr Tyr Ser
                565                 570                 575

Thr Glu Arg Lys Thr Asn Ser Leu Pro Leu His Ser Val Lys Ser Ile
                580                 585                 590

Lys Ser Asp Phe Ile Asp Lys Ala Glu Glu Ser Thr Gln Ser Lys Glu
            595                 600                 605

Ile Ser Leu Pro Glu Val Ser Leu Leu Lys Ile Leu Lys Leu Asn Lys
        610                 615                 620

Pro Glu Trp Pro Phe Val Val Leu Gly Thr Leu Ala Ser Val Leu Asn
625                 630                 635                 640
```

-continued

Gly Thr Val His Pro Val Phe Ser Ile Ile Phe Ala Lys Ile Ile Thr
             645                 650                 655

Met Phe Gly Asn Asn Asp Lys Thr Thr Leu Lys His Asp Ala Glu Ile
             660                 665                 670

Tyr Ser Met Ile Phe Val Ile Leu Gly Val Ile Cys Phe Val Ser Tyr
             675                 680                 685

Phe Met Gln Gly Leu Phe Tyr Gly Arg Ala Gly Glu Ile Leu Thr Met
             690                 695                 700

Arg Leu Arg His Leu Ala Phe Lys Ala Met Leu Tyr Gln Asp Ile Ala
705                  710                 715                 720

Trp Phe Asp Glu Lys Glu Asn Ser Thr Gly Leu Thr Ile Leu
                     725                 730                 735

Ala Ile Asp Ile Ala Gln Ile Gln Gly Ala Thr Gly Ser Arg Ile Gly
             740                 745                 750

Val Leu Thr Gln Asn Ala Thr Asn Met Gly Leu Ser Val Ile Ile Ser
             755                 760                 765

Phe Ile Tyr Gly Trp Glu Met Thr Phe Leu Ile Leu Ser Ile Ala Pro
770                  775                 780

Val Leu Ala Val Thr Gly Met Ile Glu Thr Ala Ala Met Thr Gly Phe
785                  790                 795                 800

Ala Asn Lys Asp Lys Gln Glu Leu Lys His Ala Gly Lys Ile Ala Thr
             805                 810                 815

Glu Ala Leu Glu Asn Ile Arg Thr Ile Val Ser Leu Thr Arg Glu Lys
             820                 825                 830

Ala Phe Glu Gln Met Tyr Glu Glu Met Leu Gln Thr Gln His Arg Asn
             835                 840                 845

Thr Ser Lys Lys Ala Gln Ile Ile Gly Ser Cys Tyr Ala Phe Ser His
             850                 855                 860

Ala Phe Ile Tyr Phe Ala Tyr Ala Ala Gly Phe Arg Phe Gly Ala Tyr
865                  870                 875                 880

Leu Ile Gln Ala Gly Arg Met Thr Pro Glu Gly Met Phe Ile Val Phe
                     885                 890                 895

Thr Ala Ile Ala Tyr Gly Ala Met Ala Ile Gly Lys Thr Leu Val Leu
             900                 905                 910

Ala Pro Glu Tyr Ser Lys Ala Lys Ser Gly Ala Ala His Leu Phe Ala
             915                 920                 925

Leu Leu Glu Lys Lys Pro Asn Ile Asp Ser Arg Ser Gln Glu Gly Lys
930                  935                 940

Lys Pro Asp Thr Cys Glu Gly Asn Leu Glu Phe Arg Glu Val Ser Phe
945                  950                 955                 960

Phe Tyr Pro Cys Arg Pro Asp Val Phe Ile Leu Arg Gly Leu Ser Leu
                     965                 970                 975

Ser Ile Glu Arg Gly Lys Thr Val Ala Phe Val Gly Ser Ser Gly Cys
             980                 985                 990

Gly Lys Ser Thr Ser Val Gln Leu Leu Gln Arg Leu Tyr Asp Pro Val
             995                1000                1005

Gln Gly Gln Val Leu Phe Asp Gly Val Asp Ala Lys Glu Leu Asn
            1010                1015                1020

Val Gln Trp Leu Arg Ser Gln Ile Ala Ile Val Pro Gln Glu Pro
            1025                1030                1035

Val Leu Phe Asn Cys Ser Ile Ala Glu Asn Ile Ala Tyr Gly Asp
            1040                1045                1050

-continued

```
Asn Ser Arg Val Val Pro Leu Asp Glu Ile Lys Glu Ala Ala Asn
    1055                1060                1065

Ala Ala Asn Ile His Ser Phe Ile Glu Gly Leu Pro Glu Lys Tyr
    1070                1075                1080

Asn Thr Gln Val Gly Leu Lys Gly Ala Gln Leu Ser Gly Gly Gln
    1085                1090                1095

Lys Gln Arg Leu Ala Ile Ala Arg Ala Leu Leu Gln Lys Pro Lys
    1100                1105                1110

Ile Leu Leu Leu Asp Glu Ala Thr Ser Ala Leu Asp Asn Asp Ser
    1115                1120                1125

Glu Lys Val Val Gln His Ala Leu Asp Lys Ala Arg Thr Gly Arg
    1130                1135                1140

Thr Cys Leu Val Val Thr His Arg Leu Ser Ala Ile Gln Asn Ala
    1145                1150                1155

Asp Leu Ile Val Val Leu His Asn Gly Lys Ile Lys Glu Gln Gly
    1160                1165                1170

Thr His Gln Glu Leu Leu Arg Asn Arg Asp Ile Tyr Phe Lys Leu
    1175                1180                1185

Val Asn Ala Gln Ser Val Gln
    1190                1195

<210> SEQ ID NO 7
<211> LENGTH: 541
<212> TYPE: PRT
<213> ORGANISM: Homo sapiens
<220> FEATURE:
<221> NAME/KEY: MISC_FEATURE
<222> LOCATION: (230)..(230)
<223> OTHER INFORMATION: Xaa at position 230 represents any L amino acid

<400> SEQUENCE: 7

Met Ile Leu Gly Ile Leu Ala Ser Leu Val Asn Gly Ala Cys Leu Pro
1               5                   10                  15

Leu Met Pro Leu Val Leu Gly Glu Met Ser Asp Asn Leu Ile Ser Gly
                20                  25                  30

Cys Leu Val Gln Thr Asn Thr Tyr Ser Phe Phe Arg Leu Thr Leu Tyr
            35                  40                  45

Tyr Val Gly Ile Gly Val Ala Ala Leu Ile Phe Gly Tyr Ile Gln Ile
        50                  55                  60

Ser Leu Trp Ile Ile Thr Ala Ala Arg Gln Thr Lys Arg Ile Arg Lys
65                  70                  75                  80

Gln Phe Phe His Ser Val Leu Ala Gln Asp Ile Gly Trp Phe Asp Ser
                85                  90                  95

Cys Asp Ile Gly Glu Leu Asn Thr Arg Met Thr Asp Ile Asp Lys Ile
            100                 105                 110

Ser Asp Gly Ile Gly Asp Lys Ile Ala Leu Leu Phe Gln Asn Met Ser
        115                 120                 125

Thr Phe Ser Ile Gly Leu Ala Val Gly Leu Val Lys Gly Trp Lys Leu
    130                 135                 140

Thr Leu Val Thr Leu Ser Thr Ser Pro Leu Ile Met Ala Ser Ala Ala
145                 150                 155                 160

Ala Cys Ser Arg Met Val Ile Ser Leu Thr Ser Lys Glu Leu Ser Ala
                165                 170                 175

Tyr Ser Lys Ala Gly Ala Val Ala Glu Glu Val Leu Ser Ser Ile Arg
            180                 185                 190

Thr Val Ile Ala Phe Arg Ala Gln Glu Lys Glu Leu Gln Arg Ser Phe
```

```
            195                 200                 205
Leu Leu Asn Ile Thr Arg Tyr Ala Trp Phe Tyr Phe Pro Gln Trp Leu
210                 215                 220

Leu Ser Cys Val Leu Xaa Phe Val Arg Tyr Thr Gln Asn Leu Lys Asp
225                 230                 235                 240

Ala Lys Asp Phe Gly Ile Lys Arg Thr Ile Ala Ser Lys Val Ser Leu
                245                 250                 255

Gly Ala Val Tyr Phe Phe Met Asn Gly Thr Tyr Gly Leu Ala Phe Trp
            260                 265                 270

Tyr Gly Thr Ser Leu Ile Leu Asn Gly Glu Pro Gly Tyr Thr Ile Gly
        275                 280                 285

Thr Val Leu Ala Val Phe Phe Ser Val Ile His Ser Ser Tyr Cys Ile
290                 295                 300

Gly Ala Ala Val Pro His Phe Glu Thr Phe Ala Ile Ala Arg Gly Ala
305                 310                 315                 320

Ala Phe His Ile Phe Gln Val Ile Asp Lys Lys Pro Ser Ile Asp Asn
                325                 330                 335

Phe Ser Thr Ala Gly Tyr Lys Pro Glu Ser Ile Glu Gly Thr Val Glu
            340                 345                 350

Phe Lys Asn Val Ser Phe Asn Tyr Pro Ser Arg Pro Ser Ile Lys Ile
        355                 360                 365

Leu Lys Gly Leu Asn Leu Arg Ile Lys Ser Gly Glu Thr Val Ala Leu
370                 375                 380

Val Gly Leu Asn Gly Ser Gly Lys Ser Thr Val Val Gln Leu Leu Gln
385                 390                 395                 400

Arg Leu Tyr Asp Pro Asp Gly Phe Ile Met Val Asp Glu Asn Asp
                405                 410                 415

Ile Arg Ala Leu Asn Val Arg His Tyr Arg Asp His Ile Gly Val Val
                420                 425                 430

Ser Gln Glu Pro Val Leu Phe Gly Thr Thr Ile Ser Asn Asn Ile Lys
        435                 440                 445

Tyr Gly Arg Asp Asp Val Thr Asp Glu Glu Met Glu Arg Ala Ala Arg
450                 455                 460

Glu Ala Asn Ala Tyr Asp Phe Ile Met Glu Phe Pro Asn Lys Phe Asn
465                 470                 475                 480

Thr Leu Val Gly Glu Lys Gly Ala Gln Met Ser Gly Gly Gln Lys Gln
                485                 490                 495

Arg Ile Ala Ile Ala Arg Ala Leu Val Arg Asn Pro Lys Ile Leu Ile
            500                 505                 510

Leu Asp Glu Ala Thr Ser Ala Leu Asp Ser Glu Ser Lys Ser Ala Val
        515                 520                 525

Gln Ala Ala Leu Glu Lys Asp Thr Pro Arg Tyr Ser Phe
530                 535                 540

<210> SEQ ID NO 8
<211> LENGTH: 514
<212> TYPE: PRT
<213> ORGANISM: Homo sapiens

<400> SEQUENCE: 8

Met Ile Leu Gly Ile Leu Ala Ser Leu Val Asn Gly Ala Cys Leu Pro
1               5                   10                  15

Leu Met Pro Leu Val Leu Gly Glu Met Ser Asp Asn Leu Ile Ser Gly
            20                  25                  30
```

-continued

```
Cys Leu Val Gln Thr Asn Thr Tyr Ser Phe Phe Arg Leu Thr Leu Tyr
         35                  40                  45

Tyr Val Gly Ile Gly Val Ala Ala Leu Ile Phe Gly Tyr Ile Gln Ile
 50                  55                  60

Ser Leu Trp Ile Ile Thr Ala Ala Arg Gln Thr Lys Arg Ile Arg Lys
 65                  70                  75                  80

Gln Phe Phe His Ser Val Leu Ala Gln Asp Ile Gly Trp Phe Asp Ser
                 85                  90                  95

Cys Asp Ile Gly Glu Leu Asn Thr Arg Met Thr Asp Ile Asp Lys Ile
                100                 105                 110

Ser Asp Gly Ile Gly Asp Lys Ile Ala Leu Leu Phe Gln Asn Met Ser
            115                 120                 125

Thr Phe Ser Ile Gly Leu Ala Val Gly Leu Val Lys Gly Trp Lys Leu
        130                 135                 140

Thr Leu Val Thr Leu Ser Thr Ser Pro Leu Ile Met Ala Ser Ala Ala
145                 150                 155                 160

Ala Cys Ser Arg Met Val Ile Ser Leu Thr Ser Lys Glu Leu Ser Ala
                165                 170                 175

Tyr Ser Lys Ala Gly Ala Val Ala Glu Glu Val Leu Ser Ser Ile Arg
            180                 185                 190

Thr Val Ile Ala Phe Arg Ala Gln Glu Lys Glu Leu Gln Arg Tyr Thr
        195                 200                 205

Gln Asn Leu Lys Asp Ala Lys Asp Phe Gly Ile Lys Arg Thr Ile Ala
    210                 215                 220

Ser Lys Val Ser Leu Gly Ala Val Tyr Phe Phe Met Asn Gly Thr Tyr
225                 230                 235                 240

Gly Leu Ala Phe Trp Tyr Gly Thr Ser Leu Ile Leu Asn Gly Glu Pro
                245                 250                 255

Gly Tyr Thr Ile Gly Thr Val Leu Ala Val Phe Phe Ser Val Ile His
            260                 265                 270

Ser Ser Tyr Cys Ile Gly Ala Ala Val Pro His Phe Glu Thr Phe Ala
        275                 280                 285

Ile Ala Arg Gly Ala Ala Phe His Ile Phe Gln Val Ile Asp Lys Lys
    290                 295                 300

Pro Ser Ile Asp Asn Phe Ser Thr Ala Gly Tyr Lys Pro Glu Ser Ile
305                 310                 315                 320

Glu Gly Thr Val Glu Phe Lys Asn Val Ser Phe Asn Tyr Pro Ser Arg
                325                 330                 335

Pro Ser Ile Lys Ile Leu Lys Gly Leu Asn Leu Arg Ile Lys Ser Gly
            340                 345                 350

Glu Thr Val Ala Leu Val Gly Leu Asn Gly Ser Gly Lys Ser Thr Val
        355                 360                 365

Val Gln Leu Leu Gln Arg Leu Tyr Asp Pro Asp Gly Phe Ile Met
    370                 375                 380

Val Asp Glu Asn Asp Ile Arg Ala Leu Asn Val Arg His Tyr Arg Asp
385                 390                 395                 400

His Ile Gly Val Val Ser Gln Glu Pro Val Leu Phe Gly Thr Thr Ile
                405                 410                 415

Ser Asn Asn Ile Lys Tyr Gly Arg Asp Asp Val Thr Asp Glu Glu Met
            420                 425                 430

Glu Arg Ala Ala Arg Glu Ala Asn Ala Tyr Asp Phe Ile Met Glu Phe
        435                 440                 445

Pro Asn Lys Phe Asn Thr Leu Val Gly Glu Lys Gly Ala Gln Met Ser
```

```
              450                 455                 460
Gly Gly Gln Lys Gln Arg Ile Ala Ile Ala Arg Ala Leu Val Arg Asn
465                 470                 475                 480

Pro Lys Ile Leu Ile Leu Asp Glu Ala Thr Ser Ala Leu Asp Ser Glu
                485                 490                 495

Ser Lys Ser Ala Val Gln Ala Ala Leu Glu Lys Asp Thr Pro Arg Tyr
                500                 505                 510

Ser Phe
```

<210> SEQ ID NO 9
<211> LENGTH: 2066
<212> TYPE: DNA
<213> ORGANISM: Homo sapiens

<400> SEQUENCE: 9

```
cgagcaaagg tcggactaca atcgtggtag cacaccgact ttctactatt cgaagtgcag      60
atttgattgt gaccctaaag gatggaatgc tggcggagaa aggagcacat gctgaactaa     120
tggcaaaacg aggtctatat tattcacttg tgatgtcaca ggatattaaa aaagctgatg     180
aacagatgga gtcaatgaca tattctactg aaagaaagac caactcactt cctctgcact     240
ctgtgaagag catcaagtca gacttcattg acaaggctga ggaatccacc caatctaaag     300
agataagtct tcctgaagtc tctctattaa aaattttaaa gttaaacaag cctgaatggc     360
cttttgtggt tctggggaca ttggcttctg ttctaaatgg aactgttcat ccagtatttt     420
ccatcatctt tgcaaaaatt ataaccatgt tggaaataa tgataaaacc acattaaagc      480
atgatgcaga aatttattcc atgatattcg tcattttggg tgttatttgc tttgtcagtt     540
atttcatgca gggattattt tacggcagag caggggaaat tttaacgatg agattaagac     600
acttggcctt caaagccatg ttatatcagg atattgcctg gtttgatgaa aaggaaaaca     660
gcacaggagg cttgacaaca atattagcca tagatatagc acaaattcaa ggagcaacag     720
gttccaggat tggcgtctta acacaaaatg caactaacat gggactttca gttatcattt     780
cctttatata tggatgggag atgacattcc tgattctgag tattgctcca gtacttgccg     840
tgacaggaat gattgaaacc gcagcaatga ctggatttgc caacaaagat aagcaagaac     900
ttaagcatgc tggaaagata gcaactgaag ctttggagaa tatacgtact atagtgtcat     960
taacaaggga aaaagccttc gagcaaatgt atgaagagat gcttcagact caacacagaa    1020
atacctcgaa gaaagcacag attattggaa gctgttatgc attcagccat gcctttatat    1080
attttgccta tgcagcaggg tttcgatttg agcctattt aattcaagct ggacgaatga    1140
ccccagaggg catgttcata gttttttactg caattgcata tggagctatg gccatcggaa    1200
aaacgctcgt tttggctcct gaatattcca agccaaatc gggggctgcg catctgtttg    1260
ccttgttgga aagaaaacca atatagaca gccgcagtca agaagggaaa aagccagaca    1320
catgtgaagg gaatttagag tttcgagaag tctctttctt ctatccatgt cgcccagatg    1380
ttttcatcct ccgtggctta tccctcagta ttgagcgagg aaagacagta gcatttgtgg    1440
ggagcagcgg ctgtgggaaa agcacttctg ttcaacttct gcagagactt tatgaccccg    1500
tgcaaggaca agtgctgttt gatggtgtgg atgcaaaaga attgaatgta cagtggctcc    1560
gttcccaaat agcaatcgtt cctcaagagc ctgtgctctt caactgcagc attgctgaga    1620
acatcgccta tggtgacaac agccgtgtgg tgccattaga tgagatcaaa gaagccgcaa    1680
atgcagcaaa tatccattct tttattgaag gtctcccctga gaatacaac acacaagttg    1740
```

```
gactgaaagg agcacagctt tctggcggcc agaaacaaag actagctatt gcaagggctc    1800
ttctccaaaa acccaaaatt ttattgttgg atgaggccac ttcagccctc gataatgaca    1860
gtgagaaggt ggttcagcat gcccttgata aagccaggac gggaaggaca tgcctagtgg    1920
tcactcacag gctctctgca attcagaacg cagatttgat agtggttctg cacaatggaa    1980
agataaagga acaaggaact catcaagagc tcctgagaaa tcgagacata tattttaagt    2040
tagtgaatgc acagtcagtg cagtga                                        2066

<210> SEQ ID NO 10
<211> LENGTH: 2856
<212> TYPE: DNA
<213> ORGANISM: Homo sapiens

<400> SEQUENCE: 10
cctaattcct ctaatatctc tctgtgagcc taaaccaata attatatatt acattctatt      60
gtctttctta taaactgca gaaagataaa tatcactttg tttgttcctg taggttttct     120
ttagtgtaat ccatagcagt tattgcattg gagcagcagt ccctcattat tgataagaaa    180
cccagtatag ataacttttc cacagctgga tataaacctg aatccataga aggaactgtg    240
gaatttaaaa atgtttcttt caattatcca tcaagaccat ctatcaagat tctgaaaggt    300
ctgaatctca gaattaagtc tggagagaca gtcgccttgg tcggtctcaa tggcagtggg    360
aagagtacgg tagtccagct tctgcagagg ttatatgatc cggatgatgg ctttatcatg    420
gtggatgaga atgacatcag agctttaaat gtgcggcatt atcgagacca tattggagtg    480
gttagtcaag agcctgtttt gttcgggacc accatcagta acaatatcaa gtatggacga    540
gatgatgtga ctgatgaaga gatggagaga gcagcaaggg aagcaaatgc gtatgatttt    600
atcatggagt ttcctaataa atttaataca ttggtagggg aaaaaggagc tcaaatgagt    660
ggagggcaga acagaggat cgcaattgct cgtgccttag ttcgaaaccc caagattctg    720
attttagatg aggctacgtc tgccctggat tcagaaagca agtcagctgt tcaagctgca    780
ctggagaagg cgagcaaagg tcggactaca atcgtggtag cacaccgact ttctactatt    840
cgaagtgcag atttgattgt gaccctaaag gatggaatgc tggcggagaa aggagcacat    900
gctgaactaa tggcaaaacg aggtctatat tattcacttg tgatgtcaca ggatattaaa    960
aaagctgatg aacagatgga gtcaatgaca tattctactg aaagaaagac caactcactt    1020
cctctgcact ctgtgaagag catcaagtca gacttcattg acaaggctga ggaatccacc    1080
caatctaaag agataagtct tcctgaagtc tctctattaa aaattttaaa gttaaacaag    1140
cctgaatggc ttttgtggt tctggggaca ttggcttctg ttctaaatgg aactgttcat    1200
ccagtatttt ccatcatctt tgcaaaaatt ataaccatgt ttggaaataa tgataaaacc    1260
acattaaagc atgatgcaga aatttattcc atgatattcg tcattttggg tgttatttgc    1320
tttgtcagtt atttcatgca ggattatttt acggcagag caggggaaat tttaacgatg    1380
agattaagac acttggcctt caaagccatg ttatatcagg atattgcctg gtttgatgaa    1440
aaggaaaaca gcacaggagg cttgacaaca atattagcca tagatatagc acaaattcaa    1500
ggagcaacag gttccaggat tggcgtctta acacaaaatg caactaacat gggactttca    1560
gttatcattt cctttatata tggatgggag atgacattcc tgattctgag tattgctcca    1620
gtacttgccg tgacaggaat gattgaaacc gcagcaatga ctggatttgc caacaaagat    1680
aagcaagaac ttaagcatgc tggaaagata gcaactgaag ctttggagaa tatacgtact    1740
atagtgtcat taacaaggga aaaagccttc gagcaaatgt atgaagagat gcttcagact    1800
```

```
caacacagaa ataccctcgaa gaaagcacag attattggaa gctgttatgc attcagccat    1860
gcctttatat attttgccta tgcagcaggg tttcgatttg gagcctattt aattcaagct    1920
ggacgaatga ccccagaggg catgttcata gttttactg caattgcata tggagctatg     1980
gccatcggaa aaacgctcgt tttggctcct gaatattcca aagccaaatc gggggctgcg    2040
catctgtttg ccttgttgga aagaaacca aatatagaca gccgcagtca agaagggaaa     2100
aagccagaca catgtgaagg gaatttagag tttcgagaag tctctttctt ctatccatgt    2160
cgcccagatg tttcatcct ccgtggctta tccctcagta ttgagcgagg aaagacagta     2220
gcatttgtgg ggagcagcgg ctgtgggaaa agcacttctg ttcaacttct gcagagactt    2280
tatgaccccg tgcaaggaca agtgctgttt gatggtgtgg atgcaaaaga attgaatgta    2340
cagtggctcc gttcccaaat agcaatcgtt cctcaagagc ctgtgctctt caactgcagc    2400
attgctgaga acatcgccta tggtgacaac agccgtgtgg tgccattaga tgagatcaaa    2460
gaagccgcaa atgcagcaaa tatccattct tttattgaag gtctccctga aaatacaac    2520 acacaagttg gactgaaagg agcacagctt tctggcggcc agaaacaaag actagctatt    2580
gcaagggctc ttctccaaaa acccaaaatt ttattgttgg atgaggccac ttcagccctc    2640
gataatgaca gtgagaaggt ggttcagcat gcccttgata aagccaggac gggaaggaca    2700
tgcctagtgg tcactcacag gctctctgca attcagaacg cagatttgat agtggttctg    2760
cacaatggaa agataaagga acaaggaact catcaagagc tcctgagaaa tcgagacata    2820
tattttaagt tagtgaatgc acagtcagtg cagtga                              2856

<210> SEQ ID NO 11
<211> LENGTH: 1175
<212> TYPE: DNA
<213> ORGANISM: Homo sapiens

<400> SEQUENCE: 11
cctaattcct ctaatatctc tctgtgagcc taaaccaata attatatatt acattctatt      60
gtctttctta taactgcaa gaaagataaa tatcactttg tttgttcctg taggttttct      120
ttagtgtaat ccatagcagt tattgcattg gagcagcagt ccctcattat tgataagaaa    180
cccagtatag ataacttttc cacagctgga tataaacctg aatccataga aggaactgtg    240
gaatttaaaa atgtttcttt caattatcca tcaagaccat ctatcaagat tctgaaaggt    300
ctgaatctca gaattaagtc tggagagaca gtcgccttgg tcggtctcaa tggcagtggg    360
aagagtacgg tagtccagct tctgcagagg ttatatgatc cggatgatgg ctttatcatg    420
gtggatgaga atgacatcag agctttaaat gtgcggcatt atcgagacca tattggagtg    480
gttagtcaag agcctgtttt gttcgggacc accatcagta acaatatcaa gtatggacga    540
gatgatgtga ctgatgaaga gatggagaga gcagcaaggg aagcaaatgc gtatgatttt    600
atcatggagt ttcctaataa atttaataca ttggtagggg aaaaaggagc tcaaatgagt    660
ggagggcaga aacagaggat cgcaattgct cgtgccttag ttcgaaaccc caagattctg    720
attttagatg aggctacgtc tgccctggat tcagaaagca agtcagctgt tcaagctgca    780
ctggagaagg atacccccag gtattcattt tgacctaatt tcacctcaag tggagaatcg    840
ctgaccttga accagcgccc ttcgacagct ctggcccctc aaacctcacc ctgacctcct    900
gctgcctatg agctactgca catacctcaa ggccatatgc agttgtggcc ctgcaccaaa    960
ttacactgaa tctaggaggg gagttggcag tggcggtatg aaaaaccatt gaacagtttt   1020
```

```
ctcgatggcc tgactcccett ataaaccaga gccttcagac cccttacaag gcttaatggc   1080
acattttact tgcatttgc ttggaagtga gttaagcgtt ttttttctc taagaaaatc      1140 gcaggcttct ttttttaaaa tgctgacttt atgga                                1175

<210> SEQ ID NO 12
<211> LENGTH: 3177
<212> TYPE: DNA
<213> ORGANISM: Homo sapiens
<220> FEATURE:
<221> NAME/KEY: misc_feature
<222> LOCATION: (198)..(198)
<223> OTHER INFORMATION: n at position 198 represents any nucleotide (A,
      T, C or G)

<400> SEQUENCE: 12
atggtcatct cattgaccag taaggaatta agtgcctatt ccaaagctgg ggctgtggca      60
gaagaagtct tgtcatcaat ccgaacagtc atagccttta gggcccagga gaaagaactt    120
caaaggtctt tccttttaaa tataacaaga tatgcttggt tttatttttcc ccagtggcta   180 ctaagttgtg ttctgttntt tgtaaggtat acacagaatc tcaaagatgc aaaggatttt    240
ggcataaaaa ggactatagc ttcaaaagtg tctcttggtg ctgtgtactt ctttatgaat    300
ggaacctatg gacttgcttt ttggtatgga acctccttga ttcttaatgg agaacctgga    360
tataccatcg ggactgttct tgctgttttc tttagtgtaa tccatagcag ttattgcatt    420
ggagcagcag tccctcactt tgaaaccttc gcaatagccc gaggagctgc ctttcatatt    480
ttccaggtta ttgataagaa acccagtata gataactttt ccacagctgg atataaacct    540
gaatccatag aaggaactgt ggaatttaaa aatgtttctt tcaattatcc atcaagacca    600
tctatcaaga ttctgaaagg tctgaatctc agaattaagt ctggagagac agtcgccttg    660
gtcggtctca atggcagtgg gaagagtacg gtagtccagc ttctgcagag gttatatgat    720
ccggatgatg gctttatcat ggtggatgag aatgacatca gagctttaaa tgtgcggcat    780
tatcgagacc atattggagt ggttagtcaa gagcctgttt tgttcgggac caccatcagt    840
aacaatatca gtatggacg agatgatgtg actgatgaag agatggagag agcagcaagg    900
gaagcaaatg cgtatgattt tatcatggag tttcctaata aatttaatac attggtaggg    960
gaaaaaggag ctcaaatgag tggagggcag aaacagagga tcgcaattgc tcgtgcctta   1020
gttcgaaacc ccaagattct gattttagat gaggctacgc ctgccctgga ttcagaaagc   1080
aagtcagctg ttcaagctgc actggagaag gcgagcaaag tcggactac aatcgtggta   1140 gcacaccgac tttctactat tcgaagtgca gatttgattg tgaccctaaa ggatggaatg   1200
ctggcggaga aaggagcaca tgctgaacta atggcaaaac gaggtctata ttattcactt   1260
gtgatgtcac aggatattaa aaaagctgat gaacagatgg agtcaatgac atattctact   1320
gaaagaaaga ccaactcact tcctctgcac tctgtgaaga gcatcaagtc agacttcatt   1380
gacaaggctg aggaatccac ccaatctaaa gagataagtc ttcctgaagt ctctctatta   1440 aaaatttaa agttaaacaa gcctgaatgg ccttttgtgg ttctggggac attggcttct   1500
gttctaaatg gaactgttca tccagtattt tccatcatct ttgcaaaaat tataaccatg   1560
tttggaaata atgataaaac cacattaaag catgatgcag aaatttattc catgatattc   1620
gtcattttgg gtgttatttg ctttgtcagt tatttcatgc agggattatt ttacggcaga   1680 gcagggggaaa ttttaacgat gagattaaga cacttggcct tcaaagccat gttatatcag   1740
gatattgcct ggtttgatga aaaggaaaac agcacaggag gcttgacaac aatattagcc   1800
```

| | | |
|---|---|---|
| atagatatag cacaaattca aggagcaaca ggttccagga ttggcgtctt aacacaaaat | 1860 | |
| gcaactaaca tgggactttc agttatcatt tcctttatat atggatggga gatgacattc | 1920 | |
| ctgattctga gtattgctcc agtacttgcc gtgacaggaa tgattgaaac cgcagcaatg | 1980 | |
| actggatttg ccaacaaaga taagcaagaa cttaagcatg ctggaaagat agcaactgaa | 2040 | |
| gctttggaga atatacgtac tatagtgtca ttaacaaggg aaaaagcctt cgagcaaatg | 2100 | |
| tatgaagaga tgcttcagac tcaacacaga aatacctcga agaaagcaca gattattgga | 2160 | |
| agctgttatg cattcagcca tgcctttata tattttgcct atgcagcagg gtttcgattt | 2220 | |
| ggagcctatt taattcaagc tggacgaatg accccagagg gcatgttcat agtttttact | 2280 | |
| gcaattgcat atggagctat ggccatcgga aaaacgctcg ttttggctcc tgaatattcc | 2340 | |
| aaagccaaat cggggggctgc gcatctgttt gccttgttgg aaaagaaacc aaatatagac | 2400 | |
| agccgcagtc aagaagggaa aaagccagac acatgtgaag ggaatttaga gtttcgagaa | 2460 | |
| gtctctttct tctatccatg tcgcccagat gttttcatcc tccgtggctt atccctcagt | 2520 | |
| attgagcgag gaaagacagt agcatttgtg gggagcagcg gctgtgggaa aagcacttct | 2580 | |
| gttcaacttc tgcagagact ttatgacccc gtgcaaggac aagtgctgtt tgatggtgtg | 2640 | |
| gatgcaaaag aattgaatgt acagtggctc cgttcccaaa tagcaatcgt tcctcaagag | 2700 | |
| cctgtgctct tcaactgcag cattgctgag aacatcgcct atggtgacaa cagccgtgtg | 2760 | |
| gtgccattag atgagatcaa agaagccgca atgcagcaga tatccattc ttttattgaa | 2820 | |
| ggtctccctg agaaatacaa cacacaagtt ggactgaaag gagcacagct ttctggcggc | 2880 | |
| cagaaacaaa gactagctat tgcaagggct cttctccaaa acccaaaat tttattgttg | 2940 | |
| gatgaggcca cttcagccct cgataatgac agtgagaagg tggttcagca tgcccttgat | 3000 | |
| aaagccagga cggaaggac atgcctagtg gtcactcaca ggctctctgc aattcagaac | 3060 | |
| gcagatttga tagtggttct gcacaatgga aagataaagg aacaaggaac tcatcaagag | 3120 | |
| ctcctgagaa atcgagacat atattttaag ttagtgaatg cacagtcagt gcagtga | 3177 | |

<210> SEQ ID NO 13
<211> LENGTH: 3702
<212> TYPE: DNA
<213> ORGANISM: Homo sapiens
<220> FEATURE:
<221> NAME/KEY: misc_feature
<222> LOCATION: (723)..(723)
<223> OTHER INFORMATION: n at position 723 represents any nucleotide (A, T, C or G)

<400> SEQUENCE: 13

| | | |
|---|---|---|
| ttccgctttg ctgatggact ggacatcaca ctcatgatcc tgggtatact ggcatcactg | 60 | |
| gtcaatggag cctgccttcc tttaatgcca ctggttttag gagaaatgag tgataacctt | 120 | |
| attagtggat gtctagtcca aactaacaca tactctttct tcaggttgac cctgtattat | 180 | |
| gttggaatag tgttgctgc cttgattttt ggttacatac agatttcctt gtggattata | 240 | |
| actgcagcac gacagaccaa gaggattcga aaacagtttt tcattcagt tttggcacag | 300 | |
| gacatcggct ggtttgatag ctgtgacatc ggtgaactta acactcgcat gacagacatt | 360 | |
| gacaaaatca gtgatggtat tggagataag attgctctgt tgtttcaaaa catgtctact | 420 | |
| ttttcgattg gcctggcagt tggtttggtg aagggctgga aactcaccct agtgactcta | 480 | |
| tccacgtctc ctcttataat ggcttcagcg gcagcatgtt ctaggatggt catctcattg | 540 | |
| accagtaagg aattaagtgc ctattccaaa gctggggctg tggcagaaga agtcttgtca | 600 | |

```
tcaatccgaa cagtcatagc ctttagggcc caggagaaag aacttcaaag gtctttcctt    660
ttaaatataa caagatatgc ttggttttat ttccccagt ggctactaag ttgtgttctg    720
ttntttgtaa ggtatacaca gaatctcaaa gatgcaaagg attttggcat aaaaaggact    780
atagcttcaa aagtgtctct tggtgctgtg tacttcttta tgaatggaac ctatggactt    840 gcttttttggt atggaaccct cttgattctt aatggagaac ctggatatac catcgggact    900
gttcttgctg ttttctttag tgtaatccat agcagttatt gcattggagc agcagtccct    960
cactttgaaa ccttcgcaat agcccgagga gctgcctttc atattttcca ggttattgat   1020
aagaaaccca gtatagataa cttttccaca gctggatata aacctgaatc catgaaagga   1080
actgtggaat ttaaaaatgt ttctttcaat tatccatcaa gaccatctat caagattctg   1140
aaaggtctga atctcagaat taagtctgga gagacagtcg ccttggtcgg tctcaatggc   1200
agtgggaaga gtacggtagt ccagcttctg cagaggttat atgatccgga tgatggcttt   1260
atcatggtgg atgagaatga catcagagct ttaaatgtgc ggcattatcg agaccatatt   1320
ggagtggtta gtcaagagcc tgttttgttc gggaccacca tcagtaacaa tatcaagtat   1380
ggacgagatg atgtgactga tgaagagatg gagagagcag caagggaagc aaatgcgtat   1440
gattttatca tggagtttcc taataaattt aatacattgg taggggaaaa aggagctcaa   1500
atgagtggag gcagaaaca gaggatcgca attgctcgtg ccttagttcg aaaccccaag   1560
attctgattt tagatgaggc tacgtctgcc ctggattcag aaagcaagtc agctgttcaa   1620
gctgcactgg agaaggcgag caaaggtcgg actacaatcg tggtagcaca ccgactttct   1680
actattcgaa gtgcagattt gattgtgacc ctaaaggatg aatgctggc ggagaaagga   1740 gcacatgctg aactaatggc aaaacgaggt ctatattatt cacttgtgat gtcacaggat   1800
attaaaaaag ctgatgaaca gatggagtca atgacatatt ctactgaaag aaagaccaac   1860
tcacttcctc tgcactctgt gaagagcatc aagtcagact tcattgacaa ggctgaggaa   1920
tccacccaat ctaaagagat aagtcttcct gaagtctctc tattaaaaat tttaaagtta   1980
aacaagcctg aatggccttt tgtggttctg gggacattgg cttctgttct aaatggaact   2040
gttcatccag tattttccat catctttgca aaaattataa ccatgtttgg aaataatgat   2100
aaaaccacat taaagcatga tgcagaaatt tattccatga tattcgtcat tttgggtgtt   2160
atttgctttg tcagttattt catgcaggga ttattttacg gcagagcagg ggaaatttta   2220
acgatgagat taagacactt ggccttcaaa gccatgttat atcaggatat tgcctggttt   2280
gatgaaaagg aaaacagcac aggaggcttg acaacaatat tagccataga tatagcacaa   2340
attcaaggag caacaggttc caggattggc gtcttaacac aaaatgcaac taacatggga   2400
ctttcagtta tcatttcctt tatatatgga tgggagatga cattcctgat tctgagtatt   2460
gctccagtac ttgccgtgac aggaatgatt gaaaccgcag caatgactgg atttgccaac   2520
aaagataagc aagaacttaa gcatgctgga agatagcaa ctgaagcttt ggagaatata   2580
cgtactatag tgtcattaac aagggaaaaa gccttcgagc aaatgtatga agagatgctt   2640
cagactcaac acagaaatac ctcgaagaaa gcacagatta ttggaagctg ttatgcattc   2700
agccatgcct ttatatattt tgcctatgca gcagggtttc gatttggagc ctatttaatt   2760
caagctggac gaatgacccc agagggcatg ttcatagttt ttactgcaat tgcatatgga   2820
gctatggcca tcggaaaaac gctcgttttg gctcctgaat attccaaagc caatcggggg   2880
gctgcgcatc tgtttgcctt gttggaaaag aaaccaaata tagacagccg cagtcaagaa   2940
gggaaaaagc cagacacatg tgaagggaat ttagagtttc gagaagtctc tttcttctat   3000
```

-continued

```
ccatgtcgcc cagatgtttt catcctccgt ggcttatccc tcagtattga gcgaggaaag    3060
acagtagcat ttgtggggag cagcggctgt gggaaaagca cttctgttca acttctgcag    3120
agactttatg accccgtgca aggacaagtg ctgtttgatg gtgtggatgc aaaagaattg    3180
aatgtacagt ggctccgttc ccaaatagca atcgttcctc aagagcctgt gctcttcaac    3240
tgcagcattg ctgagaacat cgcctatggt gacaacagcc gtgtggtgcc attagatgag    3300
atcaaagaag ccgcaaatgc agcaaatatc cattctttta ttgaaggtct ccctgagaaa    3360
tacaacacac aagttggact gaaaggagca cagctttctg gcggccagaa acaaagacta    3420
gctattgcaa gggctcttct ccaaaaaccc aaaattttat tgttggatga ggccacttca    3480
gccctcgata atgacagtga aaggtggtt cagcatgccc ttgataaagc caggacggga    3540
aggacatgcc tagtggtcac tcacaggctc tctgcaattc agaacgcaga tttgatagtg    3600
gttctgcaca atggaaagat aaaggaacaa ggaactcatc aagagctcct gagaaatcga    3660
gacatatatt ttaagttagt gaatgcacag tcagtgcagt ga                       3702
```

<210> SEQ ID NO 14
<211> LENGTH: 3621
<212> TYPE: DNA
<213> ORGANISM: Homo sapiens

<400> SEQUENCE: 14

```
ttccgctttg ctgatggact ggacatcaca ctcatgatcc tgggtatact ggcatcactg      60
gtcaatggag cctgccttcc tttaatgcca ctggttttag gagaaatgag tgataacctt     120
attagtggat gtctagtcca aactaacaca tactcttcct tcaggttgac cctgtattat     180
gttggaatag tgttgctgc cttgattttt ggttacatac agatttcctt gtggattata     240
actgcagcac gacagaccaa gaggattcga aaacagtttt tcattcagt tttggcacag     300 gacatcggct ggtttgatag ctgtgacatc ggtgaactta acactcgcat gacagacatt     360
gacaaaatca gtgatggtat tggagataag attgctctgt tgtttcaaaa catgtctact     420
ttttcgattg gcctggcagt tggtttggtg aagggctgga aactcaccct agtgactcta     480
tccacgtctc ctcttataat ggcttcagcg gcagcatgtt ctaggatggt catctcattg     540
accagtaagg aattaagtgc ctattccaaa gctgggctg tggcagaaga agtcttgtca     600
tcaatccgaa cagtcatagc cttagggcc caggagaaag aacttcaaag gtatacacag     660
aatctcaaag atgcaaagga ttttggcata aaaaggacta tagcttcaaa agtgtctctt     720
ggtgctgtgt acttctttat gaatggaacc tatggacttg ctttttggta tggaaccctcc    780 ttgattctta atggagaacc tggatatacc atcgggactg tcttgctgt tttctttagt    840 gtaatccata gcagttattg cattggagca gcagtccctc actttgaaac cttcgcaata    900
gccccgagga gctgccttcca tattttccag gttattgata agaaacccag tatagataac    960
ttttccacag ctggatataa acctgaatcc atagaaggaa ctgtggaatt taaaaatgtt    1020
tctttcaatt atcatcaag accatctatc aagattctga aaggtctgaa tctcagaatt    1080
aagtctggag agacagtcgc cttggtcggt ctcaatggca gtgggaagag tacggtagtc    1140
cagcttctgc agaggttata tgatccggat gatggcttta tcatggtgga tgagaatgac    1200
atcagagctt taaatgtgcg gcattatcga gaccatattg gagtggttag tcaagagcct    1260
gttttgttcg ggaccaccat cagtaacaat atcaagtatg gacagatgga tgtgactgat    1320
gaagagatgg agagagcagc aaggggaagca aatgcgtatg atttatcat ggagtttcct    1380
```

```
aataaattta atacattggt aggggaaaaa ggagctcaaa tgagtggagg gcagaaacag      1440
aggatcgcaa ttgctcgtgc cttagttcga aaccccaaga ttctgatttt agatgaggct      1500
acgtctgccc tggattcaga aagcaagtca gctgttcaag ctgcactgga gaaggcgagc      1560
aaaggtcgga ctacaatcgt ggtagcacac cgactttcta ctattcgaag tgcagatttg      1620
attgtgaccc taaaggatgg aatgctggcg gagaaaggag cacatgctga actaatggca      1680
aaacgaggtc tatattattc acttgtgatg tcacaggata ttaaaaaagc tgatgaacag      1740
atggagtcaa tgacatattc tactgaaaga aagaccaact cacttcctct gcactctgtg      1800
aagagcatca agtcagactt cattgacaag gctgaggaat ccacccaatc taaagagata      1860
agtcttcctg aagtctctct attaaaaatt ttaaagttaa acaagcctga atggcctttt      1920
gtggttctgg ggacattggc ttctgttcta aatggaactg ttcatccagt attttccatc      1980
atctttgcaa aaattataac catgtttgga aataatgata aaaccacatt aaagcatgat      2040
gcagaaattt attccatgat attcgtcatt ttgggtgtta tttgctttgt cagttatttc      2100
atgcagggat tattttacgg cagagcaggg gaaattttaa cgatgagatt aagacacttg      2160
gccttcaaag ccatgttata tcaggatatt gcctggtttg atgaaaagga aaacagcaca      2220
ggaggcttga caacaatatt agccatagat atagcacaaa ttcaaggagc aacaggttcc      2280
aggattggcg tcttaacaca aaatgcaact aacatgggac tttcagttat catttccttt      2340
atatatggat gggagatgac attcctgatt ctgagtattg ctccagtact tgccgtgaca      2400
ggaatgattg aaaccgcagc aatgactgga tttgccaaca agataagca agaacttaag      2460 catgctggaa agatagcaac tgaagctttg gagaatatac gtactatagt gtcattaaca      2520
agggaaaaag ccttcgagca aatgtatgaa gagatgcttc agactcaaca cagaaatacc      2580
tcgaagaaag cacagattat tggaagctgt tatgcattca gccatgcctt tatatatttt      2640
gcctatgcag cagggtttcg atttggagcc tatttaattc aagctggacg aatgaccccca      2700 gagggcatgt tcatagtttt tactgcaatt gcatatggag ctatggccat cggaaaaacg      2760
ctcgttttgg ctcctgaata ttccaaagcc aaatcggggg ctgcgcatct gtttgccttg      2820
ttggaaaaga aaccaaatat agacagccgc agtcaagaag ggaaaaagcc agacacatgt      2880
gaagggaatt tagagtttcg agaagtctct ttcttctatc catgtcgccc agatgttttc      2940
atcctccgtg gcttatccct cagtattgag cgaggaaaga cagtagcatt tgtggggagc      3000
agcggctgtg ggaaaagcac ttctgttcaa cttctgcaga gactttatga ccccgtgcaa      3060
ggacaagtgc tgtttgatgg tgtggatgca aaagaattga atgtacagtg gctccgttcc      3120
caaatagcaa tcgttcctca agagcctgtg ctcttcaact gcagcattgc tgagaacatc      3180
gcctatggtg acaacagccg tgtggtgcca ttagatgaga tcaaagaagc cgcaaatgca      3240
gcaaatatcc attctttat tgaaggtctc cctgagaaat acaacacaca agttggactg      3300
aaaggagcac agctttctgg cggccagaaa caaagactag ctattgcaag ggctcttctc      3360
caaaaaccca aaattttatt gttggatgag gccacttcag ccctcgataa tgacagtgag      3420
aaggtggttc agcatgccct tgataaagcc aggacgggaa ggacatgcct agtggtcact      3480
cacaggctct ctgcaattca gaacgcagat ttgatagtgg ttctgcacaa tggaaagata      3540
aaggaacaag gaactcatca agagctcctg agaaatcgag acatatattt taagttagtg      3600
aatgcacagt cagtgcagtg a                                                3621
```

<210> SEQ ID NO 15
<211> LENGTH: 2021

```
<212> TYPE: DNA
<213> ORGANISM: Homo sapiens
<220> FEATURE:
<221> NAME/KEY: misc_feature
<222> LOCATION: (723)..(723)
<223> OTHER INFORMATION: n at position 723 represents any nucleotide (A,
      T, C or G)

<400> SEQUENCE: 15
ttccgctttg ctgatggact ggacatcaca ctcatgatcc tgggtatact ggcatcactg      60
gtcaatggag cctgccttcc tttaatgcca ctggttttag gagaaatgag tgataacctt     120
attagtggat gtctagtcca aactaacaca tactctttct tcaggttgac cctgtattat     180
gttggaatag gtgttgctgc cttgattttt ggttacatac agatttcctt gtggattata     240
actgcagcac gacagaccaa gaggattcga aaacagtttt tcattcagt tttggcacag      300
gacatcggct ggtttgatag ctgtgacatc ggtgaactta acactcgcat gacagacatt     360
gacaaaatca gtgatggtat tggagataag attgctctgt tgtttcaaaa catgtctact     420
ttttcgattg gcctggcagt tggtttggtg aagggctgga aactcaccct agtgactcta     480
tccacgtctc ctcttataat ggcttcagcg gcagcatgtt ctaggatggt catctcattg     540
accagtaagg aattaagtgc ctattccaaa gctggggctg tggcagaaga agtcttgtca     600
tcaatccgaa cagtcatagc ctttagggcc caggagaaag aacttcaaag gtctttcctt     660
ttaaatataa caagatatgc ttggtttat ttttccccagt ggctactaag ttgtgttctg      720
ttntttgtaa ggtatacaca gaatctcaaa gatgcaaagg attttggcat aaaaaggact     780
atagcttcaa aagtgtctct tggtgctgtg tacttcttta tgaatggaac ctatggactt     840
gcttttggt atggaaccctc cttgattctt aatggagaac ctggatatac catcgggact      900
gttcttgctg ttttctttag tgtaatccat agcagttatt gcattggagc agcagtccct     960
cactttgaaa ccttcgcaat agcccgagga gctgcctttc atattttcca ggttattgat    1020
aagaaaccca gtatagataa cttttccaca gctggatata aacctgaatc catagaagga    1080
actgtggaat ttaaaaatgt ttctttcaat tatccatcaa gaccatctat caagattctg    1140
aaaggtctga atctcagaat taagtctgga gagacagtcg ccttggtcgg tctcaatggc    1200
agtgggaaga gtacggtagt ccagcttctg cagaggttat atgatccgga tgatggcttt    1260
atcatggtgg atgagaatga catcagagct ttaaatgtgc ggcattatcg agaccatatt    1320
ggagtggtta gtcaagagcc tgttttgttc gggaccacca tcagtaacaa tatcaagtat    1380
ggacgagatg atgtgactga tgaagagatg gagagagcag caagggaagc aaatgcgtat    1440
gattttatca tggagtttcc taataaattt aatacattgg taggggaaaa aggagctcaa    1500
atgagtggag ggcagaaaca gaggatcgca attgctcgtg ccttagttcg aaaccccaag    1560
attctgattt tagatgaggc tacgtctgcc ctggattcag aaagcaagtc agctgttcaa    1620
gctgcactgg agaaggatac ccccaggtat tcattttgac ctaatttcac ctcaagtgga    1680
gaatcgctga ccttgaacca gcgcccttcg acagctctgg cccctcaaac ctcaccctga    1740
cctcctgctg cctatgagct actgcacata cctcaaggcc atatgcagtt gtggccctgc    1800
accaaattac actgaatcta ggaggggagt tggcagtggc ggtatgaaaa accattgaac    1860
agttttctcg atggcctgac tcccttataa accagagcct tcagacccct tacaaggctt    1920
aatggcacat tttactttgc atttgcttgg aagtgagtta agcgtttttt tttctctaag    1980
aaaatcgcag gcttcttttt ttaaaatgct gactttatgg a                        2021
```

<210> SEQ ID NO 16
<211> LENGTH: 1939
<212> TYPE: DNA
<213> ORGANISM: Homo sapiens

<400> SEQUENCE: 16

```
ttccgctttg ctgatggact ggacatcaca ctcatgatcc tgggtatact ggcatcactg      60
gtcaatggag cctgccttcc tttaatgcca ctggttttag gagaaatgag tgataacctt     120
attagtggat gtctagtcca aactaacaca tactctttct tcaggttgac cctgtattat     180
gttggaatag gtgttgctgc cttgattttt ggttacatac agatttcctt gtggattata     240
actgcagcac gacagaccaa gaggattcga aaacagtttt tcattcagt tttggcacag      300
gacatcggct ggtttgatag ctgtgacatc ggtgaactta acactcgcat gacagacatt     360
gacaaaatca gtgatggtat tggagataag attgctctgt tgtttcaaaa catgtctact     420
ttttcgattg gcctggcagt tggtttggtg aagggctgga aactcaccct agtgactcta     480
tccacgtctc ctcttataat ggcttcagcg gcagcatgtt ctaggatggt catctcattg     540
accagtaagg aattaagtgc ctattccaaa gctggggctg tggcagaaga agtcttgtca     600
tcaatccgaa cagtcatagc ctttaggggcc caggagaaag aacttcaaag gtatacacag     660
aatctcaaag atgcaaagga ttttggcata aaaaggacta agcttcaaaa gtgtctcttg     720
gtgctgtgta cttctttatg aatggaacct atggacttgc ttttttggtat ggaacctcct     780
tgattcttaa tggagaacct ggatatacca tcgggactgt tcttgctgtt ttctttagtg     840
taatccatag cagttattgc attggagcag cagtccctca cttttgaaacc ttcgcaatag     900
cccgaggagc tgcctttcat attttccagg ttattgataa gaaacccagt atagataact     960
tttccacagc tggatataaa cctgaatcca tagaaggaac tgtggaattt aaaaatgttt    1020
ctttcaatta tccatcaaga ccatctatca agattctgaa aggtctgaat ctcagaatta    1080
agtctggaga gacagtcgcc ttggtcggtc tcaatggcag tgggaagagt acggtagtcc    1140
agcttctgca gaggttatat gatccggatg atggctttat catggtggat gagaatgaca    1200
tcagagcttt aaatgtgcgg cattatcgag accatattgg agtggttagt caagagcctg    1260
ttttgttcgg gaccaccatc agtaacaata tcaagtatgg acgagatgat gtgactgatg    1320
aagagatgga gagcagca agggaagcaa atgcgtatga tttttatcatg gagttttccta    1380
ataaatttaa tacattggta ggggaaaaag gagctcaaat gagtggaggg cagaaacaga    1440
ggatcgcaat tgctcgtgcc ttagttcgaa accccaagat tctgattta gatgaggcta    1500
cgtctgccct ggattcagaa agcaagtcag ctgttcaagc tgcactggag aaggatccc     1560
ccaggtattc attttgacct aatttcacct caagtggaga atcgctgacc ttgaaccagc    1620
gcccttcgac agctctggcc cctcaaacct caccctgacc tcctgctgcc tatgagctac    1680
tgcacatacc tcaaggccat atgcagttgt ggccctgcac caaattacac tgaatctagg    1740
aggggagttg gcagtggcgg tatgaaaaac cattgaacag ttttctcgat ggcctgactc    1800
cctatataaac cagagccttc agaccccctta caaggcttaa tggcacattt tactttgcat    1860
ttgcttggaa gtgagttaag cgttttttttt tctctaagaa aatcgcaggc ttctttttt     1920
aaaatgctga ctttatgga                                                 1939
```

<210> SEQ ID NO 17
<211> LENGTH: 15
<212> TYPE: PRT
<213> ORGANISM: Homo sapiens

```
<400> SEQUENCE: 17

Leu Ser Gly Gly Gln Lys Gln Arg Ile Ala Ile Ala Arg Ala Leu
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: Synthetic peptide

<400> SEQUENCE: 18

Cys Gly Thr Ser Leu Ile Leu Asn Gly Glu Pro Gly Tyr Thr Ile
1               5                   10                  15

<210> SEQ ID NO 19
<211> LENGTH: 17
<212> TYPE: PRT
<213> ORGANISM: Artificial sequence
<220> FEATURE:
<223> OTHER INFORMATION: Synthetic peptide

<400> SEQUENCE: 19

Arg Phe Gly Ala Tyr Leu Ile Gln Ala Gly Arg Met Thr Pro Glu Gly
1               5                   10                  15

Cys
```

GENE ENCODING A MULTIDRUG RESISTANCE HUMAN P-GLYCOPROTEIN HOMOLOGUE ON CHROMOSOME 7P15-21 AND USES THEREOF

RELATED APPLICATIONS

This application is a continuation and claims the benefit under 35 U.S.C. §120 of U.S. application Ser. No. 13/279,549, entitled "GENE ENCODING A MULTIDRUG RESISTANCE HUMAN P-GLYCOPROTEIN HOMOLOGUE ON CHROMOSOME 7P15-21 AND USES THEREOF (FRANK)" filed on Oct. 24, 2011, which is herein incorporated by reference in its entirety. Application Ser. No. 13/279,549 claims the benefit under 35 U.S.C. §120 of U.S. application Ser. No. 12/273,849, now U.S. Pat. No. 8,076,091, granted Dec. 13, 2011, entitled "GENE ENCODING A MULTIDRUG RESISTANCE HUMAN P-GLYCOPROTEIN HOMOLOGUE ON CHROMOSOME 7P15-21 AND USES THEREOF (FRANK)" filed on Nov. 19, 2008, which is herein incorporated by reference in its entirety. Application Ser. No. 12/273,849 claims the benefit under 35 U.S.C. §120 of U.S. application Ser. No. 10/952,328, now U.S. Pat. No. 7,465,554, granted Dec. 16, 2008, entitled "GENE ENCODING A MULTIDRUG RESISTANCE HUMAN P-GLYCOPROTEIN HOMOLOGUE ON CHROMOSOME 7P15-21 AND USES THEREOF (FRANK)" filed on Sep. 29, 2004, which is herein incorporated by reference in its entirety. Application Ser. No. 10/952,328 claims the benefit under 35 U.S.C. §120 of U.S. application Ser. No. 09/873,409, now U.S. Pat. No. 6,846,883, granted Jan. 25, 2005, entitled "GENE ENCODING A MULTIDRUG RESISTANCE HUMAN P-GLYCOPROTEIN HOMOLOGUE ON CHROMOSOME 7P15-21 AND USES THEREOF" filed on Jun. 5, 2001, which is herein incorporated by reference in its entirety. Application Ser. No. 09/873,409 claims priority under 35 U.S.C. §119(e) to U.S. Provisional Application Ser. No. 60/208,913, entitled "GENE ENCODING A MULTIDRUG RESISTANCE HUMAN P-GLYCOPROTEIN HOMOLOGUE ON CHROMOSOME 7P15-21 AND USES THEREOF (FRANK)" filed on Jun. 5, 2000, which is herein incorporated by reference in its entirety.

FIELD OF INVENTION

The invention relates to genetic sequences encoding proteins which exhibit structural and functional features characteristic of P-glycoprotein family members associated with cancer multidrug resistance, immune regulatory functions, and unique functions in human pluripotent stem cells and other tissue progenitor cells. The invention encompasses substantially pure proteins, therapeutic treatments and diagnostic uses related to these proteins.

BACKGROUND OF INVENTION

P-glycoprotein, an adenosine triphosphate (ATP)-dependent drug efflux pump, is overexpressed in multidrug-resistant (MDR) tumor cells. It reduces the intracellular concentration of cytotoxic xenobiotics, thereby decreasing the effectiveness of many cancer chemotherapeutic regimens. P-glycoprotein belongs to the ABC (ATP-binding cassette) superfamily of active transporters, and is encoded by a multigene family in higher eukaryotes. Mammalian P-glycoprotein family members can be divided into three classes. Class I and class II P-glycoproteins confer multidrug resistance whereas class III proteins do not.

In humans, P-glycoprotein is encoded by two linked genes ("MDR1" and "MDR3") on chromosome 7g21.1. MDR3 functions as a lipid translocase and mutations in this gene are associated with familial intrahepatic cholestasis. MDR1 confers drug resistance on certain cancer cells. In addition to being overexpressed in cancer cells, MDRI P-glycoprotein is widely expressed in normal, predominantly secretory and absorptive human tissues, where it functions in diverse physiologic processes including cellular differentiation, cell proliferation and cell survival. In these normal cell types, P-glycoprotein functions in the transmembrane release or uptake of xenobiotics and certain therapeutic drugs, small peptide molecules, certain steroid compounds, and phospholipids.

P-glycoprotein is also expressed by lymphoid cell populations from human bone marrow and the peripheral blood. Specifically, P-glycoprotein has been shown to be expressed on the membrane of pluripotent stem cells, monocytes, dendritic cells, CD4+ and CD8+ T lymphocytes, natural killer cells, and B lymphocytes. In immune cells, P-glycoprotein functions in the transport of cytokines and other small molecules, which are critical for physiologic immune responses to occur. Specific blockade of P-glycoprotein can suppress the immune response to alloantigen and nominal antigen. However, a degree of redundancy exists for P-glycoprotein function in these cell types, pointing to the existence of additional, hitherto unidentified related molecules.

Pluripotent stem cells and other tissue progenitor cells also possess a unique P-glycoprotein-like activity, characterized by decreased intracellular accumulation of fluorescent dyes, which allows for the specific isolation of these cell types for therapeutic uses. However, it is thought that this function is not mediated by MDR1 P-glycoprotein, but rather by a related, as yet unidentified, P-glycoprotein family member.

Despite the irrefutable role of MDR1 P-glycoprotein in cancer multidrug resistance, attempts to improve chemotherapy by inhibiting this protein have met with only limited success. Thus, it may be inferred that there are homologous proteins that, like MDR1, are able to make cells resistant to therapeutic agents. In addition, it may be inferred that MDR1 homologous proteins serve P-glycoprotein-like functions in physiologic human tissues, in particular in cells of the immune system, pluripotent stem cells and tissue progenitor cells, where either redundancy exists for MDR1 P-glycoprotein function, or where MDR1 P-glycoprotein is known to not promote the observed P-glycoprotein-associated activity.

SUMMARY OF INVENTION

The invention is directed to a new member of the human P-glycoprotein family of genes located on chromosome 7p15-2, encoding proteins which confer the multidrug resistant phenotype to tumor cells and/or serve critical physiologic functions in normal human tissues.

An examination of the structure of the new gene indicates that it encodes two semiautonomous homologous halves, each with their own transmembrane and ATP-binding domains. By alternative splicing and differential gene expression and/or posttranscriptional and posttranslational modifications, the new P-glycoprotein gene can encode several distinct P-glycoproteins:

The protein of SEQ ID NO:1 (amino acids 1-659) is encoded by 14 exons (SEQ ID NO:9) of human genomic DNA from clone AC005060 on chromosome 7p15-21 and is made up of 5 transmembrane domains and one ATP-binding domain.

The protein of SEQ ID NO:2 (amino acids 1-812) is encoded by 19 exons (SEQ ID NO:10) of human genomic DNA from the contiguous clones AC002486 and AC005060 (AC002486 is the clone sequenced to the left of clone AC005060) on chromosome 7p15-21 and is made up of 5 transmembrane domains and two ATP-binding domains, of which the first is located on the N-terminal side of transmembrane domain #1, and the second on the C-terminal side of transmembrane domain #5 of the protein, on the opposite side of the plasma membrane. The protein of SEQ ID NO:2 can also be expressed as a result of transsplicing of the mRNA (SEQ ID NO: 9) encoding the protein of SEQ ID NO:1 and mRNA (SEQ ID NO: 11) encoding the protein of SEQ ID NO:3 described hereafter. In addition, the protein of SEQ ID NO:2 may be expressed as a result of posttranslational processing of the proteins of SEQ ID NO:1 and NO:3.

The protein of SEQ ID NO:3 (amino acids 1-131) is encoded by 6 exons (SEQ ID NO:11) of human genomic DNA from clone AC002486 on chromosome 7p15-21 and is made up of one ATP-binding domain and no transmembrane domains.

The protein of SEQ ID NO:4 (amino acids 1-1058) is encoded by exons (SEQ ID NO:12) of human genomic DNA from the contiguous clones AC002486 and AC005060 on chromosome 7p15-21 and is made up of 8 transmembrane domains and two ATP-binding domains, of which the first is located between transmembrane domains #3 and #4, and the second on the C-terminal side of transmembrane domains #8; on the opposite side of the plasma membrane.

The protein of SEQ ID NO:5 (amino acids 1-1222) is encoded by 23 exons (SEQ ID NO:13) of human genomic DNA from the contiguous clones AC002486 and AC005060 on chromosome 7p15-21 and is made up of 12 transmembrane domains and two ATP-binding domains, of which the first is located between transmembrane domains #7 and #8, and the second on the C-terminal side of transmembrane domain #12, on the opposite side of the plasma membrane.

The protein of SEQ ID NO:6 (amino acids 1-1195) is encoded by 24 exons (SEQ ID NO:14) of human genomic DNA from the contiguous clones AC002486 and AC005060 on chromosome 7p15-21 and is made up of 11 transmembrane domains and two ATP-binding domains, of which the first is located between transmembrane domains #6 and #7, and the second on the C-terminal side of transmembrane domain #11, on the opposite side of the plasma membrane.

The protein of SEQ ID NO:7 (amino acids 1-541) is encoded by 10 exons (SEQ ID NO:15) of human genomic DNA from clone AC002486 on chromosome 7p15-21 and is made up of 7 transmembrane domains and one ATP-binding domain on the C-terminal side of transmembrane domain #7P.

The protein of SEQ ID NO:8 (amino acids 1-514) is encoded by 11 exons (SEQ ID NO:16) of human genomic DNA from clone AC002486 on chromosome 7p15-21 and is made up of 6 transmembrane domains and one ATP-binding domain on the C-terminal side of transmembrane domain #6.

Cancer multidrug resistance may result from the expression of any of the proteins of SEQ ID NO:1, NO:2, NO:3, NO:4, NO:5, NO:6 NO:7 and NO:8. The proteins encoded by the 7p15-21 P-glycoprotein gene of the present invention may be used as markers for identifying cells likely to display multidrug resistance and can serve as targets in the design of new therapies for cancer patients. It will be understood that, except as otherwise indicated, reference to the P-glycoprotein of the present invention also includes any of the proteins of SEQ ID NO:1, NO:2, NO:3, NO:4, NO:5, NO:6, NO:7 and NO:8 as well.

The 7p15-21 P-glycoprotein confers chemoresistance to multiple chemotherapeutic agents, including cisplatinum, by mediating cellular drug efflux. Hence, specific blockade of this efflux function, for example by means of specific monoclonal antibody inhibition, can enhance intracellular drug accumulation and, as a result, drug toxicity and tumor cell killing. In addition, since 7p15-21 P-glycoprotein is functional in tumor cell proliferation, tumor growth can be therapeutically inhibited by administration of blocking specific monoclonal antibodies, even in the absence of concurrent chemotherapeutic agents. Among the proteins encoded by the 7p15-21 P-glycoprotein gene, the proteins of SEQ ID NO: 1, NO:2, NO:3, NO:4, NO:5 and NO:6 are distinct from the proteins of SEQ ID NO:7 and NO:8 in that they are selectively expressed in certain cancer cells but not in non-cancerous normal tissues. Furthermore, the proteins of SEQ ID NO:1, NO:2, NO:3, NO:4, NO:5 and NO:6 are expressed preferentially in those cancers which exhibit the highest degrees of chemoresistance to chemotherapeutic drugs, such as for example human malignant melanoma. Because of their selective expression in certain cancers but not in normal tissues, the proteins of SEQ ID NO:1, NO:2, NO:3, NO:4, NO:5 and NO:6 can be therapeutically targeted not only via inhibition of cytotoxic drug efflux or inhibition of tumor proliferation by specific monoclonal antibodies, but also by additional means, including tumor-specific cell killing mediated by cell toxin-conjugated specific monoclonal antibodies, or by therapeutic administration to afflicted patients of tumor antigen-specific vaccine preparations.

The proteins of SEQ ID NO:7 and NO:8 encoded by the 7p15-21 gene can also be expressed in certain non-cancerous normal human tissues. The invention thus provides for additional uses as relating to the function of these select proteins in physiologic tissues. Among those normal tissues, the proteins of SEQ ID NO:7 and SEQ ID NO:8 are preferentially expressed at high levels in pluripotent stem cells and other tissue progenitor cells, where they function in the transmembrane transport of xenobiotics and other small molecules. The invention provides thus for means to specifically detect and enrich these stem cells, and progenitor cells from cell mixtures and preparations in which they are contained, by detection of the cells with labeled specific monoclonal antibodies.

The proteins of SEQ ID NO:7 and NO:8 are also expressed to a certain degree in most other normal human tissues, including in cells of the immune system such as T cells, monocytes and differentiated antigen presenting cells, where they function in the efflux of cytokines and the uptake of small molecules including peptides and antigen, thus serving a critical role for the integrity of normal immune responses. When these functions are inhibited, for example by specific monoclonal antibody blockade, the normal immune response can be modulated, which can be utilized in the prevention and/or the therapy of allograft rejection in clinical organ transplantation, and also in various autoimmune diseases such as rheumatoid arthritis and multiple sclerosis. In addition, when expressed in human immune cells and other human tissues such as the endothelium of the blood-brain barrier and the epithelia of the gastrointestinal tract and the kidney, blockade of the protein can furthermore be therapeutically employed to selectively alter the uptake and secretion, and hence the pharmacological distribution, pharmacokinetics and therapeutic efficacy of those, exogenously administered therapeutic drugs which are substrates of said proteins.

In a first aspect, the invention is directed to substantially pure proteins consisting essentially of the amino acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The term "consisting essentially of" is meant to encompass proteins having exactly the same amino acid sequences, as well as proteins with insubstantially different sequences, as evidenced by their possessing the same basic functional properties. A "substantially purified" isoform is one that has been separated from other accompanying biological components and will typically comprise at least 85% of a sample, with greater percentages being preferred. Many means are available for assessing the purity of a protein within a sample, including analysis by polyacrylamide gel electrophoresis, chromatography and analytical centrifugation. A preferred method for assessing purity is by Western blotting using an antibody directed against epitopes of the 7p15-21 P-glycoprotein of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. The invention also encompasses "MDR peptides" which are defined herein as consisting of a sequence element of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 of at least 10 and preferably at least 15 or 20 residues. These may be used in the generation of antibodies. It is stipulated that an MDR peptide cannot have a sequence that is the same as any set of 10 to 15 contiguous residues in the sequence LSGGQKQRIAIARAL (SEQ ID NO:17). These proteins and MDR peptides may also be administered therapeutically to cancer patients afflicted with 7p15-21 P-glycoprotein expressing tumors, as a tumor vaccine to elicit an endogenous immune response directed against these tumors, to result in tumor-specific cell killing.

In another embodiment, the invention is directed to an antibody made by a process comprising the step of administering to an animal host a protein encoded by SEQ ID NO: 1, SEQ ID NO:2, SEQ ID NO:3, SEQ ID NO:4, SEQ ID NO:5, SEQ ID NO:6, SEQ ID NO:7 or SEQ ID NO:8, or an MDR peptide as described above. The protein or peptide should be administered to the animal at a dosage sufficient to induce antibody formation. Antibodies may be monoclonal or polyclonal. In the latter case, antibodies are preferably produced by injecting a pharmaceutically acceptable preparation into a mouse, followed by fusing mouse spleen cells with myeloma cells using techniques known in the art. The antibodies obtained should bind selectively to the proteins of SEQ ID NO: 1, SEQ ID NO:2, SEQ ID NO:3, SEQ ID NO:4, SEQ ID NO:5, SEQ ID NO:6, SEQ ID NO:7 or SEQ ID NO:8. Selective binding, in this context, means that an antibody has at least a 100-fold greater affinity for one or more of these proteins than for any other protein normally found in human cells.

The invention is also directed to a substantially pure polynucleotide consisting essentially of a nucleotide sequence encoding the proteins of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or an MDR peptide. Preferably, the polynucleotide consists essentially of the nucleotide sequence of SEQ ID NO:9, SEQ ID NO:10, SEQ ID NO:11, SEQ ID NO: 12, SEQ ID NO: 13, SEQ ID NO: 14, SEQ ID NO: 15 or SEQ ID NO: 16. The invention includes expression vectors comprising a distinct coding element consisting of these polynucleotides; and host cells transformed with such vectors. A "distinct coding element" refers to the portion of an expression vector responsible for determining the amino acid sequence of an expressed protein. The invention comprises all such elements producing proteins corresponding to the amino acid sequences shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, as well as other proteins having substantially the same structure and function.

The invention includes recombinant protein made by host cells transformed by an expression vector as discussed above. The recombinant protein may be isolated using standard techniques, including affinity chromatography with antibodies against epitopes of 7p15-21 P-glycoprotein. Preferably, the polynucleotide used in vectors for expressing such a recombinant P-glycoprotein consists essentially of the nucleotide sequences of SEQ ID NO:9, SEQ ID NO:10, SEQ ID NO:11, SEQ ID NO:12, SEQ ID NO:13, SEQ ID NO:14, SEQ ID NO:15 or SEQ ID NO:16. Oligonucleotides complementary to SEQ ID NO:9, SEQ ID NO:10, SEQ ID NO:11, SEQ ID NO:12, SEQ ID NO: 13, SEQ ID NO: 14, SEQ ID NO: 15 or SEQ ID NO: 16 and at least 15 nucleotides in length may be used as antisense inhibitors. These may be administered to patients undergoing cancer chemotherapy to increase the effectiveness of cytotoxic drugs. The in vivo transfection of cells has been known for many years and may be accomplished using viral vectors (see e.g., U.S. Pat. No. 6,020,191); liposomes (see e.g., Nicolau, Meth. Enzymol 149:157-176 (1987)); DNA complexed to agents that facilitate cellular uptake (see e.g., U.S. Pat. No. 5,264,618; WO 98/14431); or even by simply injecting naked DNA (see e.g., U.S. Pat. No. 5,693,622). Any of these procedures may be used to deliver the antisense oligonucleotides of the present invention.

The invention is also directed to a method for determining whether a cancer cell will respond to therapies aimed at reversing multidrug resistance by measuring the expression of the genes encoding the proteins of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. This method may be used to detect the existence of the multidrug resistant phenotype in cancer cells or to track the development of multidrug resistance over time by monitoring changes in gene expression in cultured cells.

In another embodiment, the invention provides for a method of determining whether a test compound inhibits multidrug resistance in cells caused by a gene encoding proteins of SEQ ID: NO:1, SEQ ID NO:2, SEQ ID NO:3, SEQ ID NO:4, SEQ ID NO:5, SEQ ID NO:6, SEQ ID NO:7 or SEQ ID NO:8. This method comprises expressing a gene encoding one or more of these polypeptides in cells that are otherwise not multidrug resistant and exposing these cells to one or more cytotoxic drugs in the presence of a test compound. Cellular survival is measured after exposure and the results obtained are compared with those from incubations carried out in essentially the same manner but in the absence of the test compound. It is concluded that the test compound inhibits multidrug resistance if cellular survival is decreased to a significant extent in incubations carried out in the presence of the test compound relative to that seen in its absence.

DETAILED DESCRIPTION

The invention is directed to a novel member of the P-glycoprotein family of drug resistance related proteins, to genetic sequences encoding this protein, to methods of determining whether a cancer cell will respond to therapies aimed at reversing P-glycoprotein mediated drug resistance, and to a method of screening test compounds for their ability to inhibit multidrug resistance. The novel P-glycoprotein gene can encode the proteins of SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

It will be understood that the invention encompasses not only sequences identical to those shown but also sequences that are essentially the same as evidenced by their retaining the same basic structural and functional characteristics. For example, techniques such as site directed mutagenesis may be used to introduce variations into a protein's structure. Variations in P-glycoprotein introduced by this or other similar methods are encompassed by the invention provided that the resulting protein retains its basic biological properties, particularly with respect to the inducement of multidrug resistance in mammalian cells.

DNA sequences encoding the proteins of the invention may be obtained from any tissue or cellular source in which they are expressed. For example, cultured cell lines may be engineered to express the P-glycoprotein gene using recombinant techniques or by continuous exposure to chemotherapeutic agents. Alternatively, sequences may be isolated from primary cells obtained from tumors.

Many methods are available for isolating DNA sequences and may be adapted for the isolation of the chromosome 7p15-21 (hereinafter "chromosome 7p") P-glycoprotein gene (see, e.g., Sambrook et al., *Molecular Cloning: A Laboratory Manual*, 2nd ed., Cold Spring Harbor Press (1989)). For example, one method is to screen a cDNA library that has been prepared by reverse transcribing mRNA isolated from tissues or cells that express the gene. The library may be prepared from, for example, human melanocyte or testis tissue and probes for screening may be synthesized based upon the sequences shown in the Sequence Listing. The probes are preferably at least 14 nucleotides long and are optimally selected from a region believed to be unique to the chromosome 7 p P-glycoprotein gene.

As an alternative, amplification of a desired sequence may be achieved by the polymerase chain reaction ("PCR") of reverse transcribed RNA. Primers for PCR may be constructed using the sequences shown in SEQ ID NO:9, SEQ ID NO:10, SEQ ID NO:11, SEQ ID NO:12, SEQ ID NO:13, SEQ ID NO:14, SEQ ID NO:15 or SEQ ID NO:16, and confirmation of the presence of chromosome 7p P-glycoprotein cDNA may be obtained by the sequencing of amplification products.

Expression of recombinant protein may be induced in a host cell by transforming it with an appropriate expression vector. The vector should contain transcriptional and translational signals recognizable by the host together with the desired structural sequence, preferably in double stranded form, in an operable linkage. For example, the P-glycoprotein DNA sequence should be positioned such that regulatory sequences present in the vector control the synthesis of mRNA and protein having the desired sequence is produced.

Preferably, nucleic acid encoding the P-glycoprotein of the invention is expressed in eukaryotic cells, especially mammalian cells. Such cells are capable of promoting post-translational modifications necessary to ensure that the recombinant protein is structurally and functionally the same as the protein isolated from, for example, multidrug resistant tumor cells. Examples of mammalian cells known to provide proper post-translational modification of cloned proteins include, inter alia, NIH-3T3 cells, CHO cells, HeLA cells, LM(tk−) cells, and the like. Eukaryotic promoters known to control recombinant gene expression are preferably utilized to drive transcription of chromosome 7p P-glycoprotein DNA, and may include that of the mouse metallothionein I gene, the TK promoter of Herpes virus, the CMV early promoter and the SV40 early promoter. Transcription may also be directed by prokaryotic promoters, such as those capable of recognizing T4 polymerase, the $P_R$ and $P_L$ promoters of bacteriophage lambda, and the trp, recA, heat shock and lacZ promoters of *E. coli*.

Expression vectors may be introduced into host cells by methods such as calcium phosphate precipitation, microinjection, electroporation or viral transfer and cells expressing the recombinant protein sequence can be selected by techniques known in the art. Confirmation of expression may be obtained by PCR amplification of P-glycoprotein sequences using primers selected from the sequences shown in SEQ ID NO:9, SEQ ID NO:10, SEQ ID NO:11, SEQ ID NO:12, SEQ ID NO:13, SEQ ID NO:14, SEQ ID NO:15 or SEQ ID NO:16.

Recombinant protein may be purified using standard techniques well known in the art. Such techniques may include filtration, precipitation, chromatography and electrophoretic methods. Purity can be assessed by performing electrophoresis on a polyacrylamide gel and visualizing proteins using standard staining methodology. Western blotting also may be performed using an antibody to chromosome 7p P-glycoprotein.

The invention is also directed to antibodies raised against the chromosome 7p P-glycoprotein. The process for producing such antibodies may involve either injecting the 7p P-glycoprotein itself into an appropriate animal or injecting short antigenic peptides made to correspond to different regions of the protein. These peptides should be at least 5 amino acids in length and should, preferably, be selected from regions believed to be unique to the 7p P-glycoprotein. Methods for generating and detecting antibodies are well known in the art, and are taught by such references as: Harlow, et al., *Antibodies, A Laboratory Manual*, Cold Spring Harbor Laboratory, NY (1988); Klein, *Immunology: The Science of Self-Nonself Discrimination*, (1982); Kennett et al., *Monoclonal Antibodies and Hybridomas: A New Dimension in Biological Analyses*, (1980); and Campbell, "Monoclonal Antibody Technology", in *Laboratory Techniques in Biochemistry and Molecular Biology*, (1984).

The term "antibody", as used herein, is meant to include intact molecules as well as fragments that retain their ability to bind antigen, such as Fab and F(ab')$_2$ fragments. The term "antibody" is also defined herein as relating to both monoclonal antibodies and polyclonal antibodies. Polyclonal antibodies are derived from the sera of animals immunized with a chromosome 7p P-glycoprotein antigen. Monoclonal antibodies to the protein can be prepared using hybridoma technology, as taught by such references as: Kohler, et al., *Nature* 256:495 (1975); and Hammerling, et al., in: *Monoclonal Antibodies and T-Cell Hybridomas* Elsevier, N.Y., pp. 563-681 (1981). In general, this technology involves immunizing an immunocompetent animal, typically a mouse, with either intact chromosome 7p P-glycoprotein or a fragment derived therefrom. Splenocytes are then extracted from the immunized animal and are fused with suitable myeloma cells, such as SP$_2$O cells. Thereafter, the resulting hybridoma cells are selectively maintained in HAT medium and then cloned by limited dilution (Wands, et al., *Gastroenterology* 80:225-232 (1981)). Cells obtained through such selection are then assayed to identify clones which secrete antibodies capable of binding chromosome 7p P-glycoprotein.

Antibodies or fragments of antibodies of the invention may be used to detect the presence of chromosome 7p P-glycoprotein in any of a variety of immunoassays. For example, antibodies may be used in radioimmunoassays or in immunometric assays, also known as "two-site" or "sandwich" assays (see Chard, "An Introduction to Radioimmune Assay and related Techniques," in: *Laboratory. Techniques in Biochemistry and Molecular Biology*, North Holland Publishing Co., NY (1978)). In a typical immunometric assay, a quantity of unlabeled antibody is bound to a solid support that is insoluble in the fluid being tested, such as blood, lymph, cellular extracts and the like. Following the initial binding of antigen to immobilized antibody, a quantity of detectably labeled second antibody (which may or may not be the same as the first) is added to permit detection and/or quantitation of bound antigen (see, e.g. *Radioimmune Assay Method*, Kirkham, et al., Ed. pp. 199-206, E&S Livingstone, Edinburgh (1970)). Many variations of these types of assays are known in the art and may be employed for the detection of 7p P-glycoprotein.

Antibodies to chromosome 7p P-glycoprotein may also be used in purification procedures (see generally, Dean et al., *Affinity Chromatography, A Practical Approach*, IRL Press (1986)). Typically, antibody is immobilized on a chromatographic matrix such as Sepharose, 4B. The matrix is then packed into a column and the preparation containing chromosome 7p P-glycoprotein is passed through under conditions that promote binding, e.g., low salt conditions. The column is then washed protein is eluted using buffer that promotes dissociation from antibody, e.g., buffer having an altered pH or salt concentration. The eluted protein may be transferred into a buffer, for example via dialysis, and thereafter either stored or used directly. Antibodies may also be used in Western blotting for the detection of chromosome 7p P-glycoprotein in a sample. For these types of assays, antibody may be used which has either been developed specifically to react with chromosome 7p P-glycoprotein or which reacts with an epitope of the protein.

The detection of the chromosome 7p P-glycoprotein may be used to determine whether tumor cells are multidrug resistant. Likewise, detection of changes in the expression of P-glycoprotein may be useful in predicting the development of multidrug resistance in cells. The cDNA of this P-glycoprotein may be useful in designing primers for diagnostic PCR, probe design for diagnostic Northern blotting, RNase protection assays, and for the design of antisense oligonucleotides complementary to the predicted cDNA for use in gene-targeting strategies for the reversal of multidrug resistance. Both in vitro and in vivo diagnostic and therapeutic uses for antisense nucleotide sequences to the chromosome 7p P-glycoprotein are envisioned.

The primary amino acid sequence and protein structure of the chromosome 7p P-glycoprotein may be utilized in the production of monoclonal antibodies (mAbs) that can be used in the diagnosis and therapy of multidrug resistant cancer. For example, synthetic peptides resembling native amino acid sequences from particular extracellular domains as determined by membrane topology prediction may be useful for developing inhibitory mAbs directed against extracellular epitopes of the chromosome 7p P-glycoprotein. Additionally, 10-20 mer synthetic peptide sequences derived from the primary amino acid sequence not included in the above-mentioned extracellular loop sequences may be useful in the development of specific diagnostic monoclonal antibodies. Specific mAbs may be employed in diagnostic FACS analysis, Western blotting, and immunohistochemistry. Such mAbs may also be employed for in vivo diagnostic uses, where label-conjugated mAbs can be used to assess tumor burden, tumor localization or residual tumor mass following chemotherapy or surgical therapy of 7p 15-21 P-glycoprotein-expressing tumors.

Specific mAbs can also be used for therapeutic purposes in cancer patients. In particular, they may be administered to reverse cancer multidrug resistance in patients receiving chemotherapeutic agents that are substrates for 7p P-glycoprotein efflux, e.g., cisplatin. In addition, specific mAbs may be used therapeutically in cancer patients for tumor-specific cell killing, either administered in an unconjugated form, resulting in immune-mediated tumor killing, or in a cell toxin-conjugated form (for example conjugated to radioactive iodine or chemical toxins), resulting in direct tumor-specific cell killing.

Specific mAbs can also be used for therapeutic purposes other than cancer multidrug resistance. Based on the predicted immunoregulatory function of 7p P-glycoprotein, these mAbs can be given to patients to prevent and/or treat organ transplant rejection, and also diverse autoimmune diseases such as rheumatoid arthritis and multiple sclerosis. Furthermore, since P-glycoproteins function in the uptake, excretion and tissue-specific distribution of a variety of pharmacological and chemical compounds, and have been implicated in mechanisms of oral bioavailability, blood/brain barrier function and renal, hepatic and biliary excretion mechanisms of several drugs, specific mAbs can be administered therapeutically to alter the pharmacokinetics and availability of those therapeutic drugs which are substrates for 7p P-glycoprotein-mediated transport function.

The compositions and methods of the present invention may have a number of uses in addition to those described above. For example, pluripotent stem cells and tissue progenitor cells such as hematopoietic stem cells, neuroprogenitor cells and muscle progenitor cells are known to possess P-glycoprotein-like efflux activities for small molecules and fluorescent dyes. Chromosome 7p P-glycoprotein may play a role in the transport of such substrates, and thus may serve as a marker for the isolation of such stem cells and progenitor cells via, for example, FACS analysis. Also, since MDR1 P-glycoprotein appears to be involved in cellular differentiation, cell proliferation, cell survival, and certain immune responses, chromosome 7p P glycoprotein, due to its homology with MDR 1 P-glycoprotein, is expected to play a role in such physiological functions as well. Thus, chromosome 7p P-glycoprotein gene and protein sequences may be useful in modulating pathophysiological disruptions of these MDR-related functions.

Examples

Since new genomic sequence information is currently being produced at a rapid pace via the human genome project, databases containing such genomic information potentially contain sequences of heretofore unidentified members of the P-glycoprotein family. Mammalian P-glycoprotein family members share characteristic amino acid sequences and protein epitopes, and assume similar conformations. Thus, a protein homology-based search was conducted in an attempt to identify novel P-glycoprotein-encoding genes. Gene-analytic and protein-analytic bioinformatics tools were utilized to further characterize the nucleic acid sequence and predicted protein structure of identified candidate genes. Specifically, the National Center for Biotechnology Information (NCBI) tblasn application was used to compare conserved amino acid sequences derived from the known structure of the human MDR1 P-glycoprotein with the NCBI non-redundant *homo sapiens* nucleotide sequence database dynamically translated in all reading frames. The signature sequence common to members of the ABC transporter family, a 15 mer amino acid sequence LSGGQKQRIAIARAL (SEQ ID NO: 17), was used to identify human genomic DNA sequences encoding homologous protein structures. Known hexamer amino acid sequences of three P-glycoprotein-specific monoclonal antibody (mAb)-binding epitopes were also employed.

Human genomic DNA clones identified in the manner described above were screened for vector contamination using the VecScreen program. Additionally, these clones were subjected to systematic homology mapping using overlapping contiguous 20-mer amino acid sequences derived from the human MDR1 protein structure and the tblasn search program. Candidate genomic DNA sequences encoding homologous amino acid sequences were compared to open reading frame (ORF) sequences predicted in each DNA clone using the NCBI ORF Finder program (Altschul, et al., *Nucleic Acids Res.* 25:3389-402 (1997)). Genomic ORFs containing homologous DNA sequences were then analyzed using the NetGene2 software package in order to predict intron splice sites in the candidate genes (Brunak et al., *J. Mol. Biol.* 220:49-65 (1991)).

A cDNA sequence was generated by conceptual linear transcription of predicted adjacent DNA exon structures. Utilizing this approach, two adjacent overlapping human genomic clones, CTA-367017 (AC002486, 79611 base pairs in length) and CTB-86D3 (AC005060, 120169 base pairs in length, sequenced to the right) were identified as forming part of an unanchored island of unknown orientation on chromosome 7p15-21. These overlapping clones were found to contain a gene sequence encoding a novel member of the human P-glycoprotein family.

In order to determine whether the predicted gene structure was expressed in human tissues, the generated cDNA sequence was compared to the human NCBI dbest non-redundant expressed sequence tags (EST) database, as described by Altschul et al., and several ESTs complementary to predicted exons from the genomic clone AC002486 were identified. Polymerase chain reaction (PCR) primers were then designed based on available sequence information in the database at the National Center for Biotechnology Information (NCBI) and the bioinformatic analysis as described above. Using these gene-specific oligonucleotide primers and the PCR technique on reverse transcribed total messenger RNA (mRNA) isolated from several human cancer cell lines and normal human tissues, including the human G3361 melanoma cell line, the MCF-7 breast carcinoma cell line, the SCC25 squamous cell carcinoma cell line, the U937 leukemia cell line, and normal peripheral blood mononuclear cells (PBMC), cDNA sequences derived from the novel 7p15-21 P-glycoprotein gene were amplified and the PCR products were subsequently sequenced using the dideoxy chain termination method on both strands.

The intron-exon structure of several gene products encoded by the 7p15-21 P-glycoprotein gene was determined by comparison of predicted and sequenced cDNA clones with genomic sequence information from the 7p15-21 P-glycoprotein gene locus (clones AC002486 and AC005060), as shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16. Protein structures encoded by the new 7p15-21 gene were then generated by conceptual amino acid translation of the predicted oligonucleotide sequences of SEQ ID NO:9, SEQ ID NO:10, SEQ ID NO:11, SEQ ID NO:12, SEQ ID NO:13, SEQ ID NO:14, SEQ ID NO:15 and SEQ ID NO:16, as shown in SEQ ID NO:1, SEQ ID NO:2, SEQ ID NO:3, SEQ ID NO:4, SEQ ID NO:5, SEQ ID NO:6, SEQ ID NO:7 and SEQ ID NO:8. These amino acid sequences were then compared with the NCBI non-redundant peptide sequence for sequence homology using the NCBI blastp program. The predicted amino acid sequences of SEQ ID NO:1, SEQ ID NO:2, SEQ ID NO:3, SEQ ID NO:4, SEQ ID NO:5, SEQ ID NO:6, SEQ ID NO:7 and SEQ ID NO:8 were also classified using the PIR-International Protein Family Classification System (Barker, et al., Nucleic Acids Res. 28:41-4 (2000); Huang et al., *Nucleic Acids Res.* 28:273-6 (2000)). Potential functional characteristics of the predicted proteins were determined by comparative analysis of the primary amino acid composition as well as by using the TMHMM1.0 software package for the prediction of transmembrane helix formation in mammalian proteins (Sonnhammer et al., *Ismb* 6:175-82 (1998)).

The novel 7p15-21 P-glycoprotein gene can encode several distinct P-glycoprotein isoforms which display 68% sequence homology with both human MDR1 and MDR3. A similar degree of homology was found with respective mouse and hamster isoforms of these human genes. Primary amino acid sequence analysis suggests that the chromosome 7p15-21 P-glycoprotein may express the C32 and anti-P-glycoprotein mAb binding epitope, but not the C219 epitope conserved in all other known P-glycoprotein isoforms (Georges, et al., *Proc. Nad Acad Sci USA* 87:152-6 (1990)).

Structural prediction revealed that the 7p15-21 P-glycoprotein gene encodes P-glycoprotein isoforms which exhibit structural similarities but also distinctive differences compared to known members of the P-glycoprotein family, as disclosed by Georges et al. For example, the protein of SEQ ID NO:2 contains two ATP-binding domains which are located on opposite sides of the plasma membrane, providing for a unique extracellular ATP-binding domain which is predicted to bind extracellular ATP. Based on these distinctive differences, it is predicted that 7p15-21 P-glycoprotein is not only involved in small molecule efflux, but that some of its isoforms are also functional in the energy-dependent uptake of small molecules. The PIR classification system confirmed the discovered chromosome 7p15-21 P-glycoprotein to be a member of the family of multidrug resistance proteins and the family of ATP-binding cassette homology superfamilies.

PCR analysis using gene-specific primers demonstrated that cDNA encoding the proteins of SEQ ID NO:1, SEQ ID NO:2, SEQ ID NO:4, SEQ ID NO:5 and SEQ ID NO:6, which in each case involves exons encoded on genomic clone AC005060, was preferentially expressed in human melanoma cells but not most other cancers tested, unlike cDNAs encoding the proteins of SEQ ID NO:7 and SEQ ID NO:8, which was found expressed in most cancers examined and also physiologic human tissues. This emphasizes that a subset of 7p 15-21 P-glycoprotein gene products can be selectively targeted in certain cancers that display particularly high degrees of chemoresistance, such as human melanoma, To assess the expression and function of 7p15-21 P-glycoprotein and the effect of specific modulation on transport function and chemoresistance, polyclonal antibodies were raised against the MDR peptides CGTSLILNGEPGYTI (SEQ ID NO:18) and RFGAYLIQAGRMTPEGC (SEQ ID NO:19), corresponding to distinct extracellular loop epitopes of 7p15-21 P-glycoprotein, by injecting mice with these antigenic peptides conjugated to the carrier substance KLH. To assess 7p15-21 P-glycoprotein surface expression of human tumor cells, indirect surface immunostaining and single color flow cytometry of freshly harvested cells was performed. To assess the effects of 7p15-21 P-gp inhibition on P-gp-mediated fluorescent dye efflux, tumor cells were incubated with anti-7p15-21 P-glycoprotein polyclonal Ab followed by addition of calcein-AM and subsequent serial cell fluorescence measurements by flow cytometry.

These studies demonstrated that P-glycoprotein is expressed on tumor cells, and that the RFGAYLIQAGRMT-PEGC (SEQ ID NO:19) epitope contained in the proteins of SEQ ID NO:1, SEQ ID NO:2, SEQ ID NO:4, SEQ ID NO:5 and SEQ ID NO:6, is preferentially expressed in human melanoma at high levels, whereas the CGTSLILNGEP-GYTI (SEQ ID NO:18) epitope, also contained in SEQ ID NO:7 and SEQ ID NO:8, is also expressed in other types of cancer and normal human cells. Antibodies against the CGTSLILNGEPGYTI (SEQ ID NO: 18) epitope inhibited both dye uptake and also dye efflux dependent on cell type, indicating a dual function of the various gene products of 7p15-21 P-glycoprotein in these distinct processes. These antibodies also enhanced cell cytotoxicity of cisplatinum in specific cell killing assays in melanoma and also breast cancer among others, indicative of their potential therapeutic usefulness in the treatment of cancer patients.

Certain cancers are known to exhibit chromosomal rearrangement in the 7p15-21 region, and such mutations can be associated with the emergence of the MDR phenotype. This raises the possibility that gene rearrangement in these cancers potentially results form episome and double minute (DM) chromosome formation during the process of gene amplification of 7p15-21 P-glycoprotein under mutagenic stresses such as chemotherapy. Cells expressing MDR1-mediated multidrug resistance are known to undergo such chromosomal rearrangements and DM chromosome formation (Scehoenlein et al., *Mol. Biol. Cell* 3:507-20 (1992); Mickley et al., *J. Clin. Invest.* 99:1947-57 (1997); Knutsen et al., *Genes Chromosomes Cancer* 23:44-54 (1998)). Thus, the chromosome 7p15-21 P-glycoprotein gene products of SEQ ID NO:1, SEQ ID NO:2, SEQ ID NO:4, SEQ ID NO:5 and SEQ ID NO:6 may be selectively overexpressed in certain cancer cells, thereby contributing to the acquired drug resistance of such cancer cells while remaining silent in normal cells. This differential expression pattern may be employed in the detection and reversal of multidrug resistance of tumorigenic mammalian cells.

What is claimed is:

1. An isolated monoclonal antibody specific for a 7p15-21 P-glycoprotein, wherein the 7p15-21 P-glycoprotein comprises SEQ ID NO:1, SEQ ID NO:2, or SEQ ID NO:3 and wherein the antibody selectively binds to SEQ ID NO:1, SEQ ID NO:2, or SEQ ID NO:3.

2. The isolated monoclonal antibody of claim 1, wherein the antibody is in cell toxin-conjugated form and is conjugated to a toxin.

3. A method of treating a subject having cancer, comprising administering to the subject an isolated monoclonal antibody of claim 1, wherein the subject has a cancer that expresses 7p15-21 P-glycoprotein and wherein the subject is treated with a cancer chemotherapy.

4. A method comprising administering a tumor vaccine comprising a 7p15-21 P-glycoprotein to a subject for the treatment of cancer, wherein the subject has a cancer that expresses 7p15-21 P-glycoprotein.

5. The method of claim 4, wherein the 7p15-21 P-glycoprotein is a protein consisting essentially of an amino acid sequence selected from the group consisting of: SEQ ID NO:1; SEQ ID NO:2; and SEQ ID NO:3.

* * * * *